(12) United States Patent
Fantuzzi

(10) Patent No.: US 11,857,743 B2
(45) Date of Patent: *Jan. 2, 2024

(54) INTERNAL BALLOON SHEATH

(71) Applicant: ABIOMED, Inc., Danvers, MA (US)

(72) Inventor: Glen Robert Fantuzzi, Danvers, MA (US)

(73) Assignee: ABIOMED, INC., Danvers, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/869,202

(22) Filed: Jul. 20, 2022

(65) Prior Publication Data

US 2023/0018110 A1    Jan. 19, 2023

Related U.S. Application Data

(63) Continuation of application No. 16/774,213, filed on Jan. 28, 2020, now Pat. No. 11,426,562.

(Continued)

(51) Int. Cl.
*A61M 25/10* (2013.01)
*A61M 25/00* (2006.01)
(Continued)

(52) U.S. Cl.
CPC ...... *A61M 25/1002* (2013.01); *A61M 3/0295* (2013.01); *A61M 25/0097* (2013.01);
(Continued)

(58) Field of Classification Search
CPC .......... A61M 25/1002; A61M 25/1006; A61M 25/0169; A61M 25/003; A61M 25/0067;
(Continued)

(56) References Cited

U.S. PATENT DOCUMENTS 5,318,532 A    6/1994  Frassica
5,403,274 A *  4/1995  Cannon ............... A61M 25/104
                                              604/9

(Continued)

FOREIGN PATENT DOCUMENTS

JP    2014104179 A    6/2014
WO       9904845 A2   2/1999

(Continued)

OTHER PUBLICATIONS

Office Action from corresponding Chinese Patent Application No. 202080022234X dated Mar. 1, 2023 (16 pages).

(Continued)

*Primary Examiner* — Robert J Utama
*Assistant Examiner* — Leah J Swanson
(74) *Attorney, Agent, or Firm* — Botos Churchill IP Law LLP

(57) ABSTRACT

A device including a sheath for insertion through an arteriotomy of a patient. The sheath comprises a tubular sheath body having a longitudinal axis, an open proximal end, an open distal end, an outer surface and an inner surface, the inner surface defining a lumen between the proximal and distal ends for passage of a catheter device. The sheath also comprises an inflatable balloon disposed within the lumen. The inflatable balloon is configured to occupy a longitudinal space in the lumen between the inner surface of the sheath body and the catheter device when the catheter device is disposed within the sheath and the inflatable balloon is inflated, and fluidically seal the lumen.

14 Claims, 15 Drawing Sheets

Related U.S. Application Data

(60) Provisional application No. 62/797,527, filed on Jan. 28, 2019.

(51) Int. Cl.
 *A61M 3/02* (2006.01)
 *A61M 25/02* (2006.01)

(52) U.S. Cl.
 CPC . *A61M 25/1034* (2013.01); *A61M 2025/0018* (2013.01); *A61M 2025/0079* (2013.01); *A61M 2025/0293* (2013.01); *A61M 2025/1081* (2013.01)

(58) Field of Classification Search
 CPC .......... A61M 25/0074; A61M 25/0075; A61M 25/0026; A61M 25/0021; A61M 25/0028; A61M 25/0029; A61M 25/0172; A61M 25/10; A61M 2025/1081; A61M 2025/0079; A61M 2025/09008; A61M 2025/0018; A61M 2025/0293; A61M 2025/09125; A61M 2025/1043; A61M 2025/104; A61M 2025/0004; A61M 2025/0006; A61M 2025/0037; A61M 2025/0039; A61M 2025/004; A61M 3/0295; A61M 2025/0025; A61M 2025/0681; A61M 2025/0059; A61M 2025/0063; A61M 2025/1047; A61M 25/1018; A61M 25/1025; A61M 25/1027; A61M 25/1034
 See application file for complete search history.

(56) References Cited

U.S. PATENT DOCUMENTS

| | | |
|---|---|---|
| 5,792,118 A | 8/1998 | Kurth et al. |
| 6,270,465 B1 | 8/2001 | Keith et al. |
| 6,447,489 B1 | 9/2002 | Peterson |
| 11,426,562 B2 * | 8/2022 | Fantuzzi ............ A61M 25/1002 |
| 2008/0065140 A1 | 3/2008 | Bonutti |
| 2013/0096604 A1 | 4/2013 | Hanson et al. |
| 2014/0171914 A1 | 6/2014 | Rowe et al. |
| 2014/0276611 A1 * | 9/2014 | Banerjee ............ A61M 25/003 604/510 |
| 2017/0197063 A1 | 7/2017 | Ahmed |

FOREIGN PATENT DOCUMENTS

| | | |
|---|---|---|
| WO | 0152754 A1 | 7/2001 |
| WO | 2008021425 A2 | 2/2008 |

OTHER PUBLICATIONS

Office Action from corresponding Indian Application No. 202117035281 dated Feb. 9, 2023 (6 pages).

International Search Report and Written Opinion for Application No. PCT/US2020/015314 dated Jun. 18, 2020.

Office Action from corresponding Chinese Patent Application No. 202080022234X dated Oct. 29, 2023 (21 pp.).

* cited by examiner

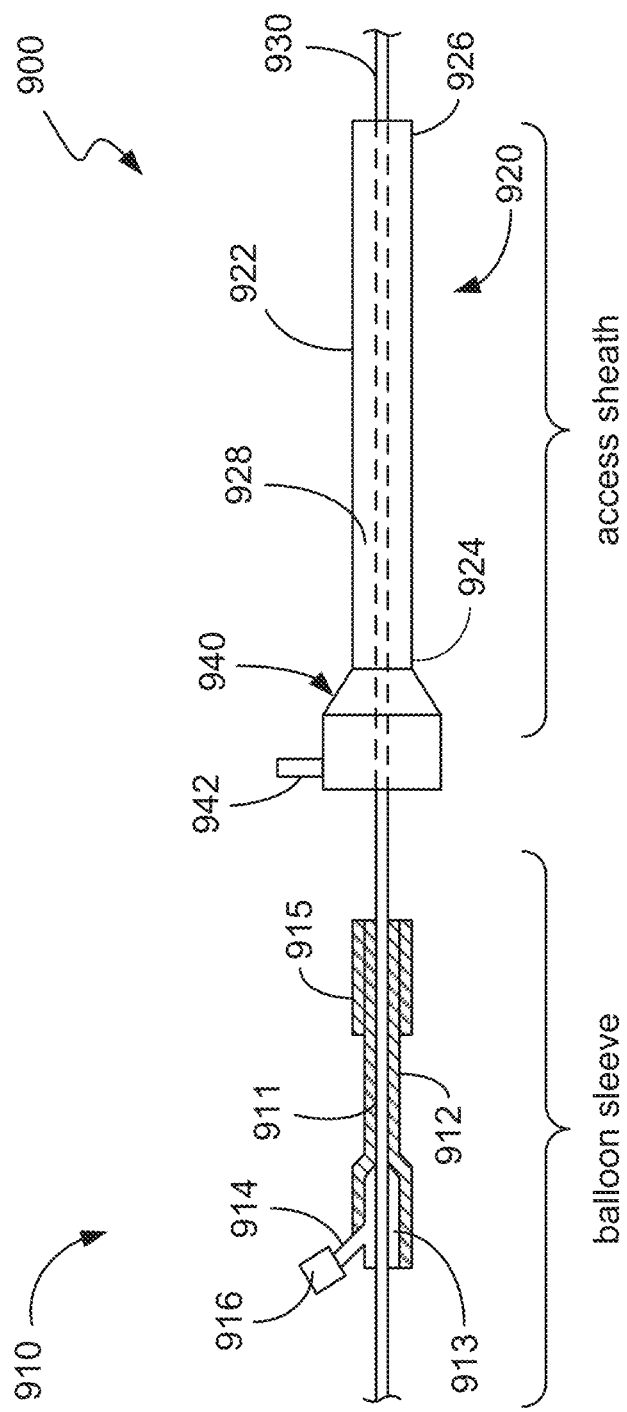
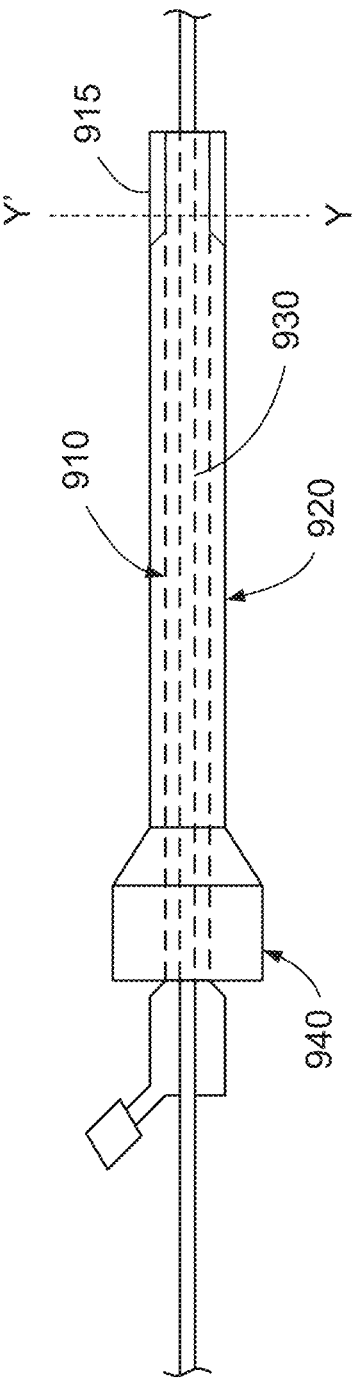
FIG. 9A
FIG. 9B

INTERNAL BALLOON SHEATH

CROSS-REFERENCE TO RELATED APPLICATIONS

This application is a continuation of U.S. patent application Ser. No. 16/774,213, filed Jan. 28, 2020, which claims the benefit of U.S. Provisional Patent Application No. 62/797,527, filed Jan. 28, 2019. The disclosures of each of the foregoing applications are hereby incorporated by reference herein in their entirety.

BACKGROUND

Intravascular medical devices may comprise, but are not limited to, an Impella® pump, an Extracorporeal Membrane Oxygenation (ECMO) pump, and a balloon pump. The Impella® pump may further comprise an Impella 2.5® pump, an Impella 5.0® pump, an Impella CP® pump and an Impella LD® pump, all of which are by Abiomed, Inc. of Danvers, MA Most intravascular medical devices are catheter devices that have an operational unit, such as a pump head, at the distal end of the catheter. Such operational units have a larger diameter compared to the catheter body supporting them. These devices often require introducer sheaths to position them in the desired location within the arteriotomy of the patient before they can be operated. The introducer sheaths are usually dimensioned such that the pump head can easily traverse through the sheath without being damaged, i.e. the inner diameter of the introducer sheath is often larger than the outer diameter of the pump head.

The difference between the inner diameter of the introducer sheath and the outer diameter of the catheter body gives rise to the development of a space between the introducer sheath and the catheter body after the pump head has been deployed from the distal end of the introducer sheath. This leads to blood ingress and stagnation within the sheath, in the space between the introducer sheath and the catheter body, which will eventually lead to clotting. When a clot forms between the sheath and intravascular medical device several issues may arise. If the clot forms at the distal tip of the sheath it may be accidentally broken free, embolizing downstream (such as, for example, into distal limb, up to right heart and lungs, etc.). The rate of occurrence of these clinical scenarios is increased when the procedure requires the device and sheath to be left in place for durations longer than several hours or at times where anticoagulation is limited.

Currently, when there is a space between the inner surface of the introducer sheath and the outer surface of the catheter of the intravascular medical device, physicians will setup the sheath so that a continuous flow of saline or heparinized saline flushes through the space, often at a flow rate of 3 cc/hr, for example. Typically this prevents clot formation, although it requires additional setup, fluid delivery to the patient, and risk of mismanagement leading to clinical complications. This issue has not been addressed by sheath manufacturers as it is assumed that introducer sheaths and the like are not for long term use. In some cases sheath manufacturers have not found a suitable technical solution, are unaware of the clinical issue, or believe the problem should be solved by the intravascular device manufacturer.

Additionally, intravascular medical devices that sit in the left ventricle across the aortic valve may be very sensitive to positioning issues. For example, if the device travels too far into or out of the heart the hemodynamic support may be compromised leading to patient harm. Long term use of an introducer sheath with an intravascular medical device threaded therethrough runs the risk of the device being dislodged from its initial position as the patient moves. Currently, physicians attempt to fix the position of the intravascular medical devices relative to the patient by coupling the proximal end of the sheath of a hub, or fixing the distal end of the device directly to the patient outside the body (for example, to the patient's skin using tape). This often requires additional geometry or design that may be bulky. In some scenarios this may be forgotten by the user and the attachment may subsequently come detached.

BRIEF SUMMARY

Disclosed herein are approaches for addressing various problems and shortcomings of the state of the art, as identified above. More particularly, disclosed herein are devices for delivery of a catheter device to an arteriotomy of a patient using a sheath with an internal balloon. In one embodiment, the sheath comprises a tubular sheath body having a longitudinal axis, an open proximal end, an open distal end, an outer surface and an inner surface, the inner surface defining a lumen between the proximal and distal ends for passage of the catheter device. The sheath also comprises an inflatable balloon configured to occupy a longitudinal space in the lumen between the inner surface of the sheath body and the catheter device when the catheter device is disposed within the sheath and the balloon is inflated, and fluidically seal the lumen.

In some implementations, the balloon may form an interference fit between the catheter device and the inner surface of the sheath body when inflated. In certain implementations, the balloon may be positioned at least at the distal end of the sheath body. In other implementations, the balloon may be positioned along the entire length of the sheath body. In further implementations, the balloon may be attached to the inner surface of the sheath body. In some implementations, the balloon may be attached at least at the distal end of the inner surface of the sheath body. In certain implementations, the balloon may be attached along the entire length of the inner surface of the sheath body. In other implementations, the balloon may be attached along at least a portion of the circumference of the sheath body. In further implementations, the balloon may be attached along at least any of the following portions of the sheath body: about 25%, about 50%, about 75%, about 100% of the inner circumference of the sheath body.

In some implementations, the inner surface of the sheath body may be pretreated to improve attachment of the balloon to the inner surface of the sheath body. In certain implementations, the balloon may be attached to the inner surface of the sheath body via heat or solvent bond. In other implementations, the inner surface of the sheath body may be pretreated via any one of: plasma activation and coronary treatment. In further implementations, the balloon may be inflated via an inflation opening located on the inner surface of the distal end of the sheath body. In some implementations, the sheath body may comprise an inflation lumen that extends from the proximal end of the sheath body to the inflation opening. In certain implementations, the inflation lumen may be in fluid communication with the inflation opening. The inflation lumen may extend along the length of the sheath body linearly or curvilinearly.

In some implementations, the sheath may further comprise a balloon sleeve on which the inflatable balloon is attached, the sleeve aligned in-line with the catheter device and configured to traverse the lumen of the sheath body. The proximal end of the balloon sleeve may comprise a hemostasis valve that seals with the catheter device. In certain implementations, the balloon sleeve may comprise an inflation lumen in fluid communication with the balloon for inflation. In other implementations, the proximal end of the balloon sleeve may comprise an inflation port in fluid communication with the inflation lumen for inflation. In further implementations, the proximal end of the sheath body may be coupled to an inflation port that is in fluid communication with the balloon for inflation. In some implementations, the inflation lumen may be in communication with a fixed volume syringe for inflation of the balloon at the proximal end of the sheath body. In certain implementations, the balloon may be inflated via the inflation port with any one of: water, saline and air.

In some implementations, the balloon may be positioned in-line with the catheter device. In other implementations, the balloon may be radially symmetric with respect to the longitudinal axis of the sheath body. In further implementations, the balloon may be ring-shaped through which the catheter device traverses. In certain implementations, the balloon may apply a radial force on the catheter device when inflated, thereby locking the catheter device in position. In some implementations, the balloon may be asymmetric with respect to the longitudinal axis of the sheath body. The balloon may exert a force on the catheter device so as to push the catheter device towards a portion of the inner surface of the sheath body when inflated, thereby locking the catheter device in position.

In certain implementations, the sheath body may comprise a lamination of a plurality of polymer layers arranged coaxially with each other about the longitudinal axis. In other implementations, the sheath body may comprise a combination of a plurality of tubular polymer layer portions arranged sequentially from the proximal to the distal end of the sheath body. Each polymer layer may comprise a different polymer material type. In some implementations, the polymer material type may comprise any one of: PEBAX® 7233SA, PEBAX® 7033SA, PEBAX® 6333SA, PEBAX® 5533SA, PEBAX® 3533SA, and PEBAX® 2533SA.

In further implementations, the sheath body may comprise reinforced structures to prevent kinking. In other implementations, the reinforced structures may comprise any one of: braids, coils and laser cut features. In some implementations, the balloon may be fabricated from any one of: urethane, polyurethane, polyethylene, polypropylene, polyethylene terephthalate (PET), polyvinyl chloride (PVC), polyethylene, cross-linked polyethylene, a polyether block amide (PEBA), and nylon. In certain implementations, the sheath body may be fabricated from any one of: a polyether block amide (such as PEBAX® or PebaSlix®), a polyethylene material, a polytetrafluoroethylene (PTFE) material, a high-density polyethylene (HDPE) material, a medium-density polyethylene (MDPE) material, and a low-density polyethylene (LDPE) material. In other implementations, the distal end of the sheath body may be fabricated from a softer elastic material than that used for the rest of the sheath body.

In further implementations, the distal end of the sheath body may comprise a smaller diameter so as to seal onto the catheter device. In some implementations, the balloon sleeve may be fabricated from any one of: urethane, polyurethane, polyethylene, polypropylene, polyethylene terephthalate (PET), polyvinyl chloride (PVC), polyethylene, cross-linked polyethylene, a polyether block amide (PEBA), and nylon.

In certain implementations, the balloon may be compliant and held flush against the inner surface of the sheath body when deflated. In other implementations, the balloon may be non-compliant and not held flush against the inner surface of the sheath body when deflated. In further implementations, the balloon may be coated with either a hydrophilic coating or a hydrophobic coating. The coating may be of a thickness that ensures appropriate balloon inflation characteristics. In some implementations, the sheath body may deform when the balloon is inflated, thereby fixing the position of the sheath in the arteriotomy of the patient.

In some implementations, the proximal end of the sheath may be coupled to a hub for manipulating the sheath as it is positioned within the arteriotomy of the patient. In certain implementations, the hub may comprise an inflation sideport that is in fluid communication with the fluid lumen, thereby enabling the attachment of a source of balloon inflation fluid. In other implementations, the hub may comprise an irrigation port that is in fluid communication with the space between the catheter device and the inner surface of the sheath body, thereby enabling the space to be flushed with fluid prior to inflation of the balloon.

In another embodiment, a sheath kit is provided. The sheath kit comprises a sheath and an inflation device coupled to the sheath. The sheath comprises a tubular sheath body having a longitudinal axis, an open proximal end, an open distal end, an outer surface and an inner surface, the inner surface defining a lumen between the proximal and distal ends for passage of the catheter device. The sheath also comprises an inflatable balloon configured to occupy a longitudinal space in the lumen between the inner surface of the sheath body and the catheter device when the catheter device is disposed within the sheath and the balloon is inflated, and fluidically seal the lumen. The inflation device comprises a fixed volume syringe filled with fluid for the inflatable balloon with the fluid.

In yet another embodiment, a method of fabricating a sheath with an internal balloon is provided. The method comprises providing a tubular sheath body, the sheath body having a longitudinal axis, an open proximal end, an open distal end, an outer surface and an inner surface, the inner surface defining a lumen between the proximal and distal ends for passage of a catheter device. The method then comprises providing an inflatable balloon positioned in the lumen, the balloon configured to occupy a space in the lumen between the inner surface of the sheath body and the catheter device when the balloon is inflated thereby fluidically sealing the lumen.

In some implementations, the method may further comprise attaching the inflatable balloon to at least a portion of the inner surface of the sheath body. In certain implementations, the method may comprise pretreating the inner surface of the sheath body to improve adhesion between the balloon and the inner surface of the sheath body. In other implementations, the pretreatment may comprise any one of: plasma activation and coronary treatment. In further implementations, the method may comprise providing a balloon sleeve for insertion into the lumen of the sheath body, the sleeve aligned in-line with the catheter device, and attaching the inflatable balloon to at least a portion of the sleeve. In some implementations, attachment of the balloon is carried out via heat or solvent bond.

In further implementations, the method may additionally comprise at least one of: (i) coating the surface of the balloon with either a hydrophilic coating or a hydrophobic coating, (ii) coating the surface of the balloon up to a predetermined coating thickness to achieve particular inflation characteristics of the balloon, and (iii) coating the catheter based medical device. In some implementations, the method may further comprise coupling a proximal end of the sheath body to a hub.

In a further embodiment, a method of using a sheath with an internal balloon for treating a patient with a catheter device is provided. The method comprises positioning a sheath in an arteriotomy of the patient. The method then comprises inserting the catheter device into the lumen to position a distal end of the catheter device in the arteriotomy of the patient. Next the method comprises flushing the space with an irrigation fluid, and inflating the balloon with an inflation fluid so as to fluidically seal the lumen.

In some implementations, the method may comprise inserting a balloon sleeve on which the inflatable balloon is attached into the lumen, the sleeve aligned in-line with the catheter device.

In another embodiment, there is provided a method of using a sheath with an internal balloon for treating a patient with a catheter device. The method comprises the steps of inserting a sheath having a lumen running therethrough into the arteriotomy of the patient. The method also comprises inserting the catheter based device into the lumen. The method then includes the step of inflating a balloon within the lumen between the sheath and the catheter based device so as to fluidically seal the lumen.

In some implementations, the method may comprise flushing the lumen prior to inflating the balloon. In certain implementations, inserting the sheath may comprise inserting a dilator into the lumen of the sheath for positioning the sheath into the arteriotomy of the patient. In some implementations, the balloon may be attached to the sheath. In other implementations, the method may further comprise inserting a balloon sleeve, onto which the balloon is attached, into the lumen of the sheath between the sheath and the catheter based device, before inflating the balloon. In further implementations, the balloon sleeve may be tightly coaxially arranged around the catheter based device.

BRIEF DESCRIPTION OF THE DRAWINGS

The foregoing and other objects and advantages will be apparent upon consideration of the following detailed description, taken in conjunction with the accompanying drawings, in which like reference characters refer to like parts throughout, and in which:

FIG. 9A shows an expanded view of an illustrative internal balloon sheath with an inline balloon sleeve according to an embodiment of the present disclosure;

FIG. 9B shows the internal balloon sheath of FIG. 9A with the inline balloon sleeve inserted into internal balloon sheath;

DETAILED DESCRIPTION

Figure 1:
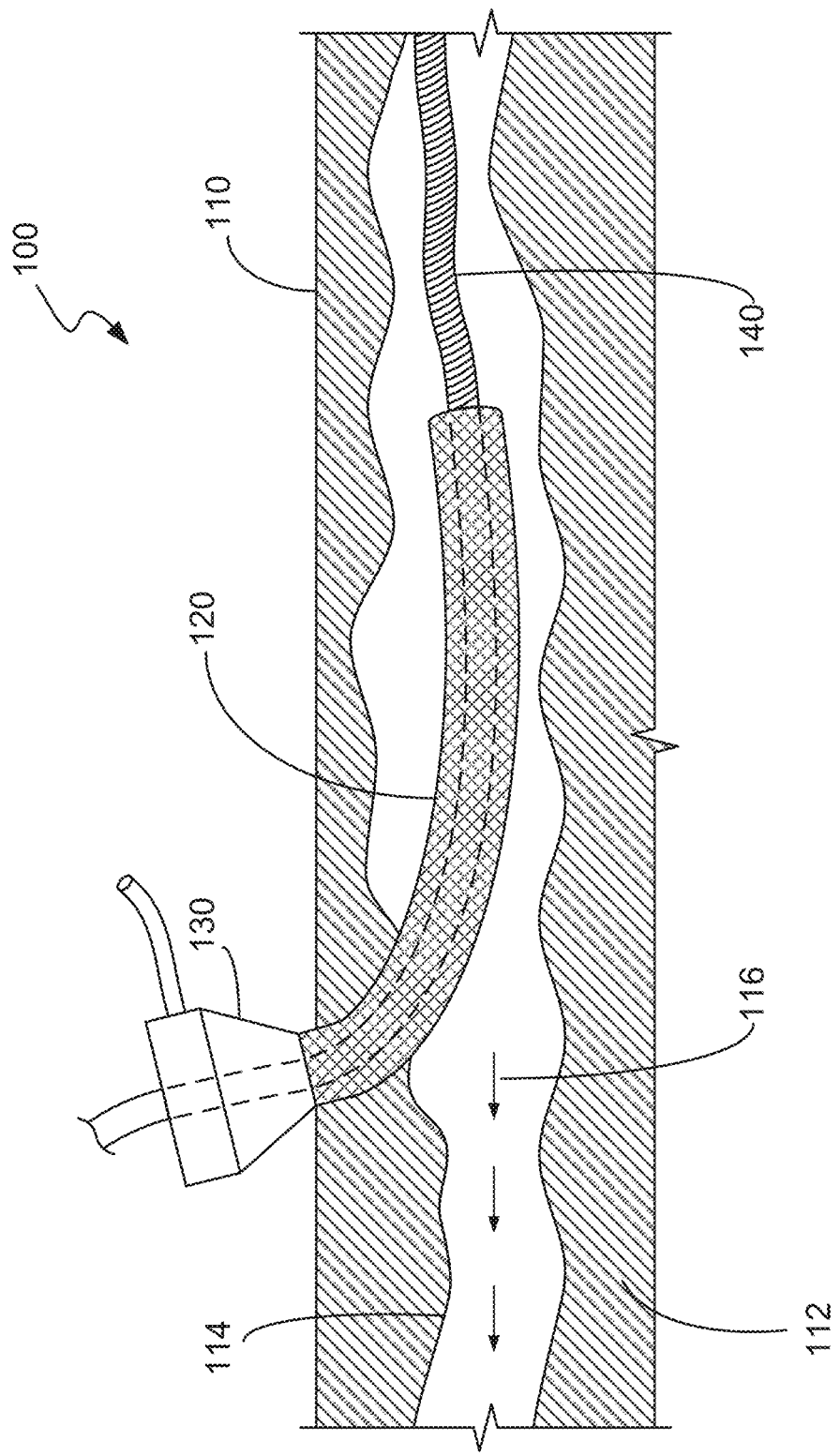
FIG. 1 shows an illustrative sheath delivery system as known in the prior art used for delivering a catheter based device into an arteriotomy of a patient.

To provide an overall understanding of the devices and methods described herein, certain illustrative embodiments will be described. Although the embodiments and features described herein are specifically described for use in connection with internal balloon sheaths for use in intravascular procedures involving catheter based ventricular assist devices, it will be understood that all the components and other features outlined below may be combined with one another in any suitable manner and may be adapted and applied to other types of procedures requiring an internal balloon sheath.

The devices and methods described herein relate to an internal balloon sheath that comprises a tubular sheath body and an inflatable balloon. The tubular sheath body comprises a longitudinal axis, an open proximal end, an open distal end, an outer surface and an inner surface, the inner surface defining a lumen between the proximal and distal ends for passage of a catheter device. The inflatable balloon is disposed within the lumen and is configured to occupy a longitudinal space in the lumen between the inner surface of the sheath body and the catheter device when the catheter device is disposed within the sheath and the balloon is inflated, and fluidically seal the lumen.

Such a sheath prevents ingress of fluid after the balloon has been inflated thereby preventing the stagnation of blood and clotting within the lumen of the sheath when the sheath is positioned within the vasculature of the patient. As the lumen within the sheath is sealed from the arteriotomy of the sheath, there is no need for the provision of a flow of irrigation fluid through the lumen of the sheath, thereby simplifying the sheath delivery system. Further, the inflated balloon forms an interference fit between the external surface of the catheter device and the inner surface of the sheath, thereby fixing or locking the position of the catheter device during use. This does away with any bulky and cumbersome fixation techniques that would be otherwise attached to the surface of the patient's skin. Additionally, as the inflatable balloon takes up any space between the catheter body and the sheath, the internal balloon sheath can be used with any size of catheter as the balloon appropriately occupies any difference in dimension within the sheath.

In some embodiments the internal balloon may be attached to at least a portion of the inner surface of the sheath body. Here the internal balloon may be attached to the inner surface of the distal end of the sheath body. Alternatively, the internal balloon may span the entire length of the sheath body and be attached to a plurality of attachment points on the inner surface of the sheath body. In certain embodiments, the balloon may be an inline radially symmetric balloon which is coaxially arranged with the sheath body such that the catheter device traverses through the balloon. In other embodiments, the balloon may be an asymmetric balloon. When inflated, the balloon forms an interference fit with the sheath and the catheter body in which the balloon grips onto the catheter thereby locking it in position.

In other embodiments the internal balloon may be attached to a balloon sleeve external to the sheath body. The sleeve may be arranged to have a tight fit over the catheter of the medical device while being slideable thereon. The sleeve may be configured such that it can be slid about the catheter and positioned within the lumen of the sheath. The balloon may be attached to the external surface of the distal end of the sleeve. Alternatively, the balloon may span the entire length of the sleeve and be attached to a plurality of attachment points on the external surface of the sleeve. In certain embodiments, the balloon may be an inline radially symmetric balloon which is coaxially arranged with the sleeve such that the catheter device traverses through the sleeve. In other embodiments, the balloon may be an asymmetric balloon. When inflated, the balloon forms an interference fit with the sheath and the catheter body in which the balloon grips onto the catheter thereby locking it in position. In other embodiments, the balloon sleeve is positioned parallel to the catheter of the medical device, thereby not requiring the medical device to be threaded through the balloon sleeve.

FIG. 1 shows a conventional sheath delivery system 100 for positioning a catheter device 140 in a blood vessel of a patient. Depicted in FIG. 1 is a sheath 120 after it has been inserted through the skin 110 and into the arteriotomy 112 of the patient. The sheath 120 is positioned in the vessel, such as a femoral artery 114, through which blood flows 116. The sheath 120 facilitates the insertion of a catheter device 140 into the artery 114. The catheter device 140 may comprise a ventricular assist device such as a percutaneous pump. An example of such a percutaneous pump is the Impella 2.5™ pump system from Abiomed, Inc. of Danvers, Massachusetts. Such pumps generally comprise a catheter body with a pump head at a distal end of the catheter body (not shown) and a handle at a proximal end of the catheter body (not shown). In most situations the pump head would have a larger diameter than the diameter of the catheter body. It will be understood that while a percutaneous heart pump is described herein, any other percutaneous or intravascular medical device can be used in conjunction with the present disclosure. The proximal end of sheath HO 120 may be coupled to a hub 130.

Figure 2:
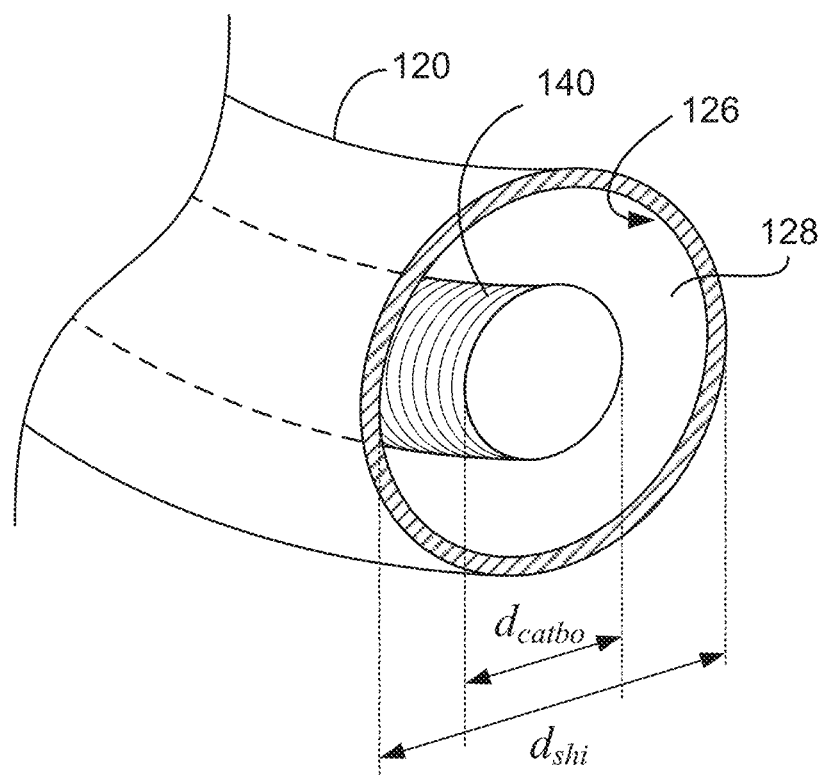
FIG. 2 shows an illustrative cross section of the sheath delivery system of FIG. 1.
Figure 3:
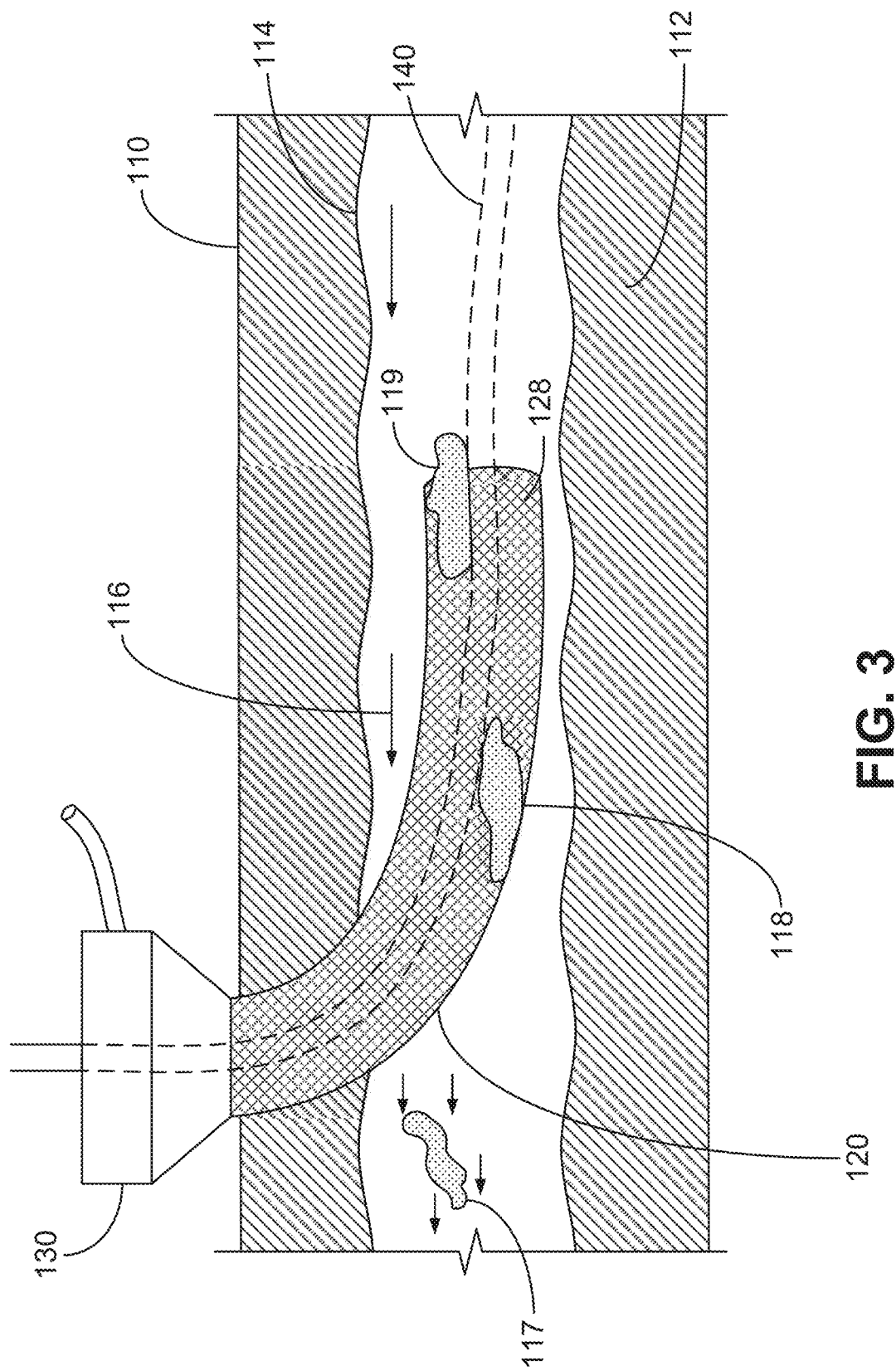
FIG. 3 shows the ingress of fluid and clots after the sheath delivery system of FIG. 1 has been inserted into the patient.

In order to facilitate traversal of the catheter device through the sheath 100, the inner diameter $d_{shi}$ of the sheath 120 is configured to be equal to or larger than an outer diameter $d_{catho}$ of the largest portion of the catheter device, i.e. $d_{shi} \geq d_{catho}$. In the case of the Impella 2.5™ pump system as exemplified in the foregoing, the largest portion of the device is the pump head. After the pump head passes through the sheath body 120, a space 128 exists between the inner surface 126 of the sheath 120 and the outer surface of the catheter device 140, as depicted in FIG. 2. This space 128 exists due to the difference in the inner diameter of the sheath $d_{shi}$ and the outer diameter of the catheter body $d_{catho}$, as shown in FIG. 2. Such a space facilitates blood ingress within the sheath 120 while the sheath body is still in the arteriotomy of the patient. As the space may not have flowing fluids within it, stagnation of blood is likely to occur which results in the formation of clots 118, 119 in the space 128 of the sheath body 120, as illustrated in FIG. 3.

Such clot formation complicates intravascular medical procedures as they may be accidentally dislodged from the sheath and freely move with the blood in the vessel (e.g., as illustrated by clot 117 in FIG. 3), embolizing downstream (such as, for example, into distal limb, up to right heart and lungs, etc.). Additionally, in some instances clot formation can increase likelihood of blocking the blood flow through the vessel. Further, once a clot begins to form it can continue to increase in size and block the lumen of the vessel. In some cases, to minimize clot formation, the sheath delivery system is provided with a flow of irrigation fluid that is fed into the lumen of the sheath 120. This flow may be provided to the lumen continuously or at a predetermined frequency, which complicates the sheath delivery system as an additional control and monitoring mechanism for such irrigation needs to be employed. Further, when the catheter device 140 is deployed the proximal end of the device may be attached to the hub 130 by tape or sutures. Such fixation may not ensure that the portion of the device within the patient's arteriotomy will not move. Additionally, such external fixation may be bulky and cumbersome, and may come loose as the patient moves.

Figure 4:
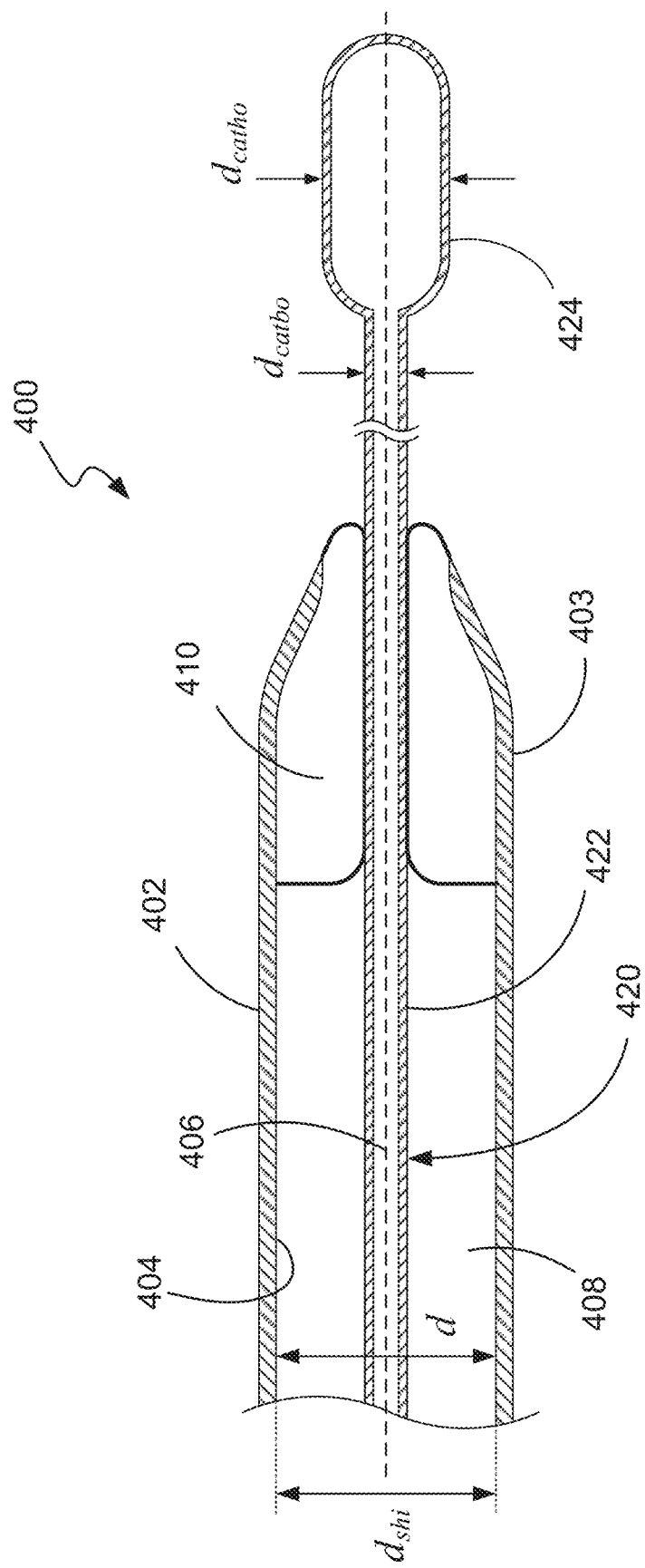
FIG. 4 shows an illustrative internal balloon sheath according to an embodiment of the present disclosure.

FIG. 4 shows an expanded view of an internal balloon sheath 400 according to an embodiment of the present disclosure. The sheath 400 is suitable for insertion into the arteriotomy of a patient, such as the femoral artery. The sheath 400 comprises a sheath body 402 having an inner surface 404 and extending along a longitudinal axis 406. The sheath body 402 comprises a lumen 408 of diameter d that extends along the longitudinal axis 406. In certain embodiments, the sheath body 402 may be tubular with a circular cross section, however the sheath body 402 may be of any shape and configuration. The sheath body 402 has an internal diameter of $d_{shi}$ and is suitable for introducing an intravascular medical device 420 into a vessel of the patient. As previously mentioned, the medical device 420 may be a catheter based device such as a percutaneous pump. An example of such a percutaneous pump is the Impella 2.5™ pump system from Abiomed, Inc. of Danvers, Massachusetts Such pumps generally comprise a catheter body 422 with a pump head 424 at a distal end of the catheter body. In most situations the pump head 424 has a larger diameter $d_{catho}$ than the diameter of the catheter body $d_{catho}$. It will be understood that while a percutaneous heart pump is described herein, any other percutaneous or intravascular medical device can be used in conjunction with the present disclosure.

Once the sheath 400 is in the correct position in the vessel, the medical device 420 is deployed from the distal end 403 of the sheath body 402. In order for the medical device 420 to emerge from the sheath 400, the internal diameter of the sheath body 402 is configured to be at least equal to the diameter of the pump head 424, i.e. $d_{shi} \geq d_{catho}$. However this means that once the medical device 420 is deployed into the vessel, the difference between the internal diameter $d_{shi}$ of the sheath body 402 and the external diameter of the catheter body $d_{catho}$ leads to a space developing that may result in the formation of clots, as described in the foregoing.

According to an embodiment of the present disclosure, an inflatable balloon 410 is positioned in the lumen 408 of the sheath body 402. In some embodiments, the balloon 410 may be positioned at the distal end 403 of the sheath body 402. In the embodiments the balloon 410 may be positioned elsewhere along the sheath body 402. In further embodiments, the balloon 410 may extend along the entire length of the sheath body 402.

The balloon 410 is configured such that it is able to assume two states and transition therebetween: a first state in which it is deflated, and a second state in which it is inflated. In the first state the balloon 410 does not come into contact with the catheter body 422 of the medical device 420, while in the second state the balloon 410 contacts the catheter body 422 of the medical device 420. In order to transition from the first state, in which the balloon 410 is deflated, to the second state, in which the balloon 410 is inflated, a fluid is supplied to the balloon 410. In some embodiments, the fluid may be air, saline or water, for example, however any biocompatible fluid may be used to inflate the balloon 410. Such fluid may be supplied to the balloon via a fluid lumen which will be described in detail in the following sections. When the balloon 410 is inflated, it reduces the diameter of the lumen 408 such that the opening in the sheath body 402 is less than the diameter of the catheter body 422 of the medical device 420, i.e. in the second state $d < d_{catho}$. As the balloon is inflated (with saline or air) it fills the void/space between the catheter body 422 and inner surface 404 of the sheath thereby preventing blood ingress, stagnation, and clotting. It should be noted that during use, after the catheter device is positioned in the arteriotomy of the patient, the lumen 408 of the sheath 400 may be first flushed with an irrigation fluid prior to inflation of the balloon 410. This removes any blood ingress that may have accumulated while the sheath 400 or the catheter device was being positioned.

In the second state the inflated balloon 410 comes into contact with the catheter body 422 of the medical device 420 and exerts a compressive force on the medical device 420. Additionally, in the second state, frictional forces between the balloon 410 and the catheter body 422 along the length of the catheter-balloon interface assist in the fixation of the position of the catheter body 422 relative to the sheath 400. In some embodiments (when the balloon 410 is not attached to the sheath 400, as will be described below), frictional forces between the balloon 410 and the inner surface 404 of the sheath body 402 along the balloon-sheath interface also assist in fixating the location of the catheter body 422 relative to the sheath 400.

While FIG. 4 shows an axially symmetric balloon 410, it will be appreciated that the balloon 410 can be of any shape or configuration. For example, the balloon 410 may be axially symmetric (as depicted in FIG. 4) in which it has a circular ring shape aligned about the longitudinal axis 406 of the sheath 400. In such a configuration, when the balloon 410 is inflated, it exerts a radial compressive force on the catheter body 422 from all directions about the longitudinal axis 406, thereby effectively gripping the catheter body 422 and locking it in position. In other embodiments, the balloon 410 may be asymmetric about the longitudinal axis 406 of the sheath 400. For example, the balloon 410 may be positioned on one side of the longitudinal axis 406 of the sheath 400. In such configurations, when the balloon 410 is inflated and assumes the second state, it exerts a compressive force on the catheter body 422 from one general direction. When that happens, the compressive force from the balloon 410 effectively pins the catheter body 422 against the inner surface 404 of the sheath body 402 and locks its position. It will be understood that when the balloon 410 is in the second state, the balloon 410 prevents any axial or radial translation of the medical device 420, thereby locking it in a fixed position.

Figure 5A:
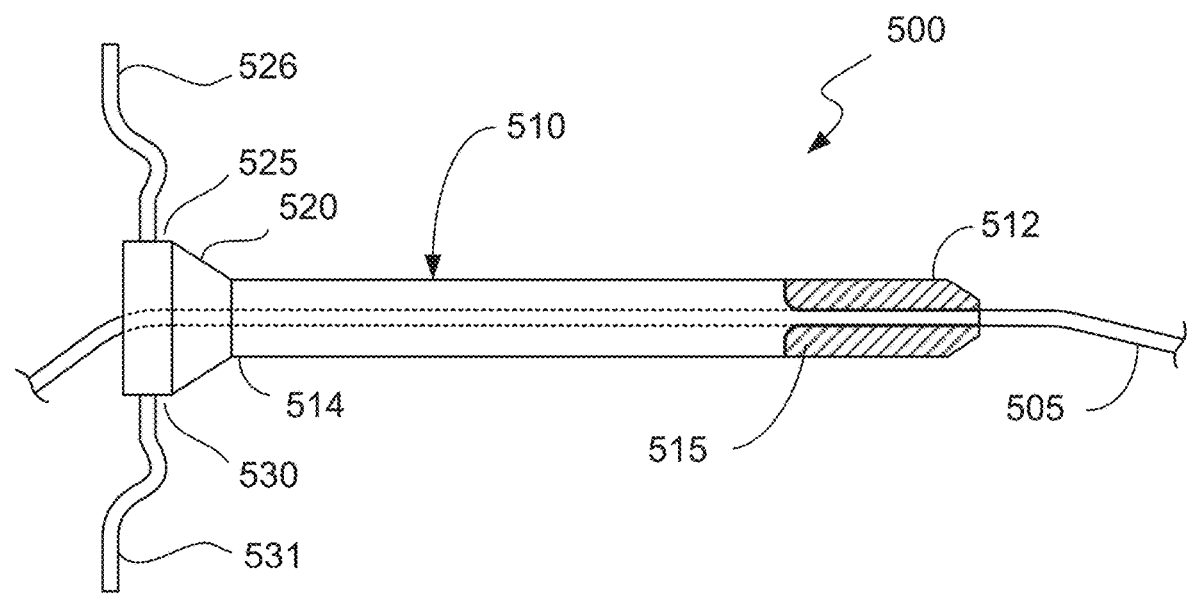
FIG. 5A shows an illustrative internal balloon sheath according to an embodiment of the present disclosure, in which the balloon is positioned at the distal end of the sheath.

FIG. 5A illustrates an exemplary internal balloon sheath 500 according to an embodiment of the present disclosure. It will be understood that the internal balloon sheath 500 has similar features to sheath 400 of FIG. 4 as described in the foregoing. Sheath 500 has a lumen for the passage of an intravascular medical device, the catheter end 505 of which is shown in FIG. 5A. Sheath 500 comprises a sheath body 510 having a distal end 512 and a proximal end 514. Sheath 500 also comprises an inflatable balloon 515 positioned within the lumen of the sheath 500 and located at the distal end 512 of the sheath body 510. In FIG. 5A, the inflatable balloon 515 has a fixed length and does not span the entire length of the sheath body 510. In some embodiments, the balloon 515 may be positioned at other locations along the sheath body 510. Further, in certain embodiments of the present disclosure, balloon 515 may be attached to the inner walls of the sheath body 510, as will be described in the following sections. Alternatively, the balloon 515 may be positioned within the sheath 500 by the insertion of a balloon sleeve into the lumen of the sheath body 510, as will be described in the following sections.

Figure 5B:
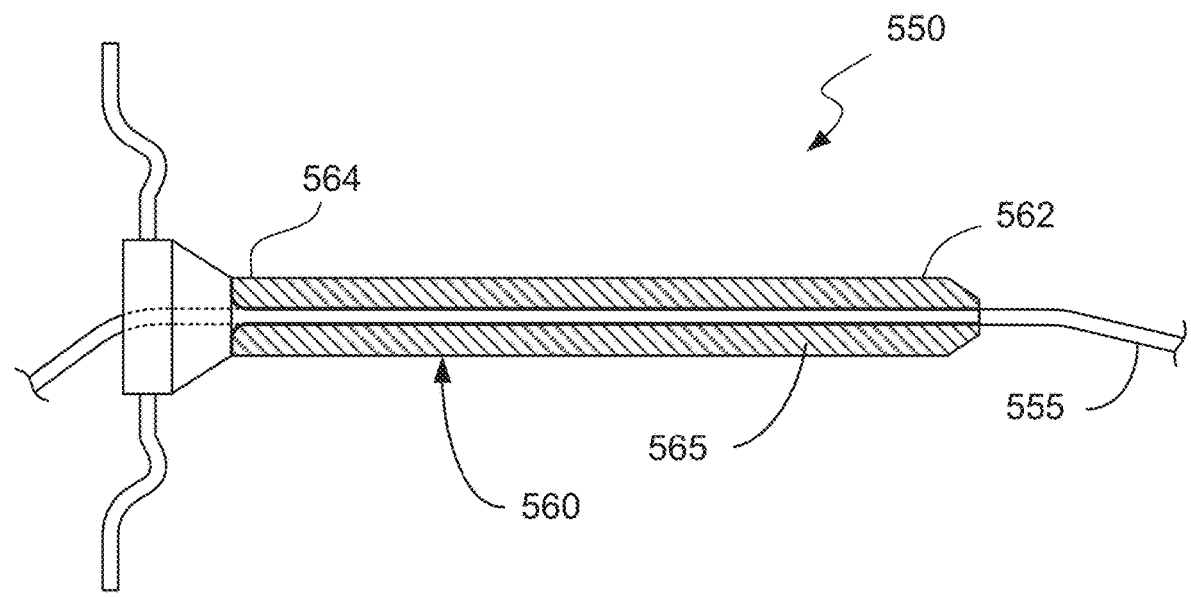
FIG. 5B shows an illustrative internal balloon sheath according to an embodiment of the present disclosure, in which the balloon is positioned along the entire length of the sheath.

FIG. 5B illustrates another exemplary internal balloon sheath 550 according to an embodiment of the present disclosure. It will be understood that the internal balloon sheath 550 has similar features to sheath 500 of FIG. 5A as described in the foregoing. Sheath 550 has a lumen for the passage of an intravascular medical device, the catheter end 555 of which is shown in FIG. 5B. As with sheath 500, sheath 550 comprises a sheath body 560 having a distal end 562 and a proximal end 564. However, in FIG. 5B, sheath 550 comprises an inflatable balloon 565 positioned within the lumen of the sheath 500, that spans the entire length of the sheath body 560. In certain embodiments of the present disclosure, balloon 565 may be attached to the inner walls of the sheath body 560, as will be described in the following sections. Alternatively, the balloon 565 may be positioned within the sheath 550 by the insertion of a balloon sleeve into the lumen of the sheath body 560, as will be described in the following sections.

According to some embodiments of the present disclosure, the balloons 510, 560 in FIGS. 5A and 5B may be axially symmetric. In other embodiments, the balloons 510, 560 may be asymmetric about the longitudinal axis of the sheath body.

As shown in FIG. 5A, the proximal end 514 of the sheath body 510 may be coupled to a hub 520. Hub 520 serves as a handle which the physician can grip while positioning the sheath 500 into the vasculature of the patient. The hub may also have features to facilitate fixation of the hub to the skin of the patient once the sheath 500 has been positioned in the vasculature of the patient. Such fixation may be via sutures or tape. Additionally, the hub 520 may have at least one sideport 525, 530. Each sideport may be connected to a flexible tube 526, 531 as shown in FIG. 5A, and, optionally, a two-way or three-way stopcock. Each sideport may be in fluid communication with the lumen of the sheath body 510. In some embodiments, the sideport may be in fluid communication with additional lumens in the sheath body 510, such as, for example, and inflation lumen as will be described in the following sections. In the embodiment of FIG. 5A, sideport 525 is in fluid communication with the lumen of the sheath body 510, while sideport 530 is in fluid communication with the inflatable balloon 515. Sideport 520 may connected to tube 526 such that irrigation fluid can be used to flush the lumen of the sheath body 510 prior to inflation of the balloon 515.

Flushing the lumen prior to inflation of the balloon 515 removes any stagnation of blood which may have collected during insertion of the sheath into the arteriotomy of the patient. Sideport 530 may connected to tube 531 such that inflation fluid can be used to inflate the balloon 515 (described below). In some embodiments, sideport 530 may be in fluid communication with the balloon 515 via a fluid lumen formed in the sheath body 510, or via internal tubing that connects the source of inflation fluid to the balloon 515. It should be noted that in the case of FIG. 5B in which the balloon 565 spans the length of the sheath body 560, there is no need for an inflation lumen within the walls of the sheath body as the proximal end of the balloon 565 may be in direct fluid communication with the inflation port on the hub.

Once in sheath 500 and hub 520 are in position, the physician may attach a saline syringe and/or pull vacuum to the sideport(s) 525, 530 to deliver fluid through the sideport up the shaft of the sheath (in the wall of the sheath body, for example, as will be described in the following sections) and into the inside of the balloon. Once the balloon 515 is inflated the physician could shut off the stopcock on the sideport to lock the volume in place.

Returning to the embodiment in FIG. 4, the balloon 410 may be attached to the inner surface 404 of the sheath body 402 and inflated and deflated therefrom. Such attachment is implemented via a heat or solvent bond. This bond is critical to ensure the balloon 410 does not rupture, during inflation, for example. In certain embodiments, the inner surface 404 of the sheath body 402 may be pretreated with plasma activation or coronary treatment to improve the likelihood of bonding the balloon 410 to the sheath body 402. In some embodiments, the balloon 410 may be located at a specific position on the sheath body 402. In such embodiments, the point of attachment of the balloon 410 may be local to the position of the balloon in the sheath 400. For example, for balloons 410 that are positioned at the distal end 403 of the sheath body 402, the point of attachment of the balloon 410 to the inner surface 404 of the sheath body 402 is at the locale of the distal end 403 of the sheath body 402.

In other embodiments, the balloon 410 may extend along the length of the sheath body 402. In such configurations, the balloon 410 may be attached to the inner surface 404 of the sheath body 402, along the entire length of balloon 410. In other configurations, the balloon 410 may only be attached to the inner surface 404 of the sheath body 402 at certain points, such as, for example, the proximal and/or distal ends of the sheath body 402. In other embodiments, the balloon 410 may not be attached to the inner surface 404 of the sheath body 402. Instead, the balloon 410 may be positioned in the lumen 408 of the sheath body 402 using a balloon sleeve, which will be described in the following sections.

As mentioned in the foregoing, and with respect to the embodiment depicted in FIG. 4, when in the first state, the balloon 410 is not inflated with fluid and does not come into contact with the catheter body 422. According to an embodiment of the present disclosure, the balloon 410 may be configured to be compliant whereby the balloon 410 sits flush and tight against a surface within the sheath 400 when in the first state. In some embodiments, this surface may be the inner wall 404 of the sheath body 402. In other embodiments, the surface on which the compliant balloon is attached may be an additional balloon sleeve (as will be detailed in the following sections). The compliant balloon 410 does not have excess balloon material when deflated and therefore allows for the unimpeded insertion and removal of medical devices 420 within the lumen 408 of the sheath body 402. Such compliant balloons may be easier to fabricate and process as there is no excess balloon material to manage during bonding of the balloon 410 to the inner surface 404 of the sheath body 402. When the compliant balloon 410 is inflated, the balloon material is elastically deformed by pressure from the inflating fluid (which, in turn, may be delivered to the balloon 410 via a syringe, for example) causing it to seal against the catheter body 422, thereby closing off the lumen to entrants from the arteriotomy (such as, for example, blood and clots).

In other embodiments, the balloon 410 may be configured to be non-compliant where the balloon is attached to a surface within the sheath 400 when in the first state. In some embodiments, this surface may be the inner wall 404 of the sheath body 402. In other embodiments, the surface on which the compliant balloon is attached may be an additional balloon sleeve (as will be detailed in the following sections). The non-compliant balloon 410 material sits within the lumen 408 of the sheath 400 when deflated (shown in FIGS. 6-8, and as described in the following sections). Non-compliant balloons may be used so that a fixed volume of fluid will always yield appropriate and predictable inflation characteristics. In some embodiments, a fixed volume syringe containing the inflation fluid may be provided with the sheath 400 to ensure the correct fluid volume of fluid is provided to the balloon 410 each time the balloon 410 is inflated. In certain embodiments, a syringe (and, optionally, a fixed volume syringe) may be provided with any of the internal balloon sheaths described in this disclosure, in a sheath kit.

With all the internal balloon sheaths of the present disclosure, it will be understood that the lumen of the internal balloon sheath is flushed with irrigation fluid to remove any blood ingress that may have occurred while positioning the sheath in the arteriotomy of the patient. After flushing the lumen, the balloon is inflated. Once the balloon is inflated, the lumen within the sheath body is sealed from the arteriotomy of the patient. It will be understood throughout this disclosure that 'seal' is to be taken to mean substantially sealing of a lumen so as to eliminate fluid flow of any amount that would enable formation of clots. Thus, unlike conventional introducer sheaths, the present disclosure does away with the need for a constant flow of irrigation fluid to flush the sheath lumen during treatment. Further, as the balloon expands so as to seal the lumen via an interference fit with the catheter of the medical device, the sheath can be used with any diameter catheter, so long as the internal diameter of the sheath body is larger than the external diameter of the most distal end of the catheter device.

Figure 6:
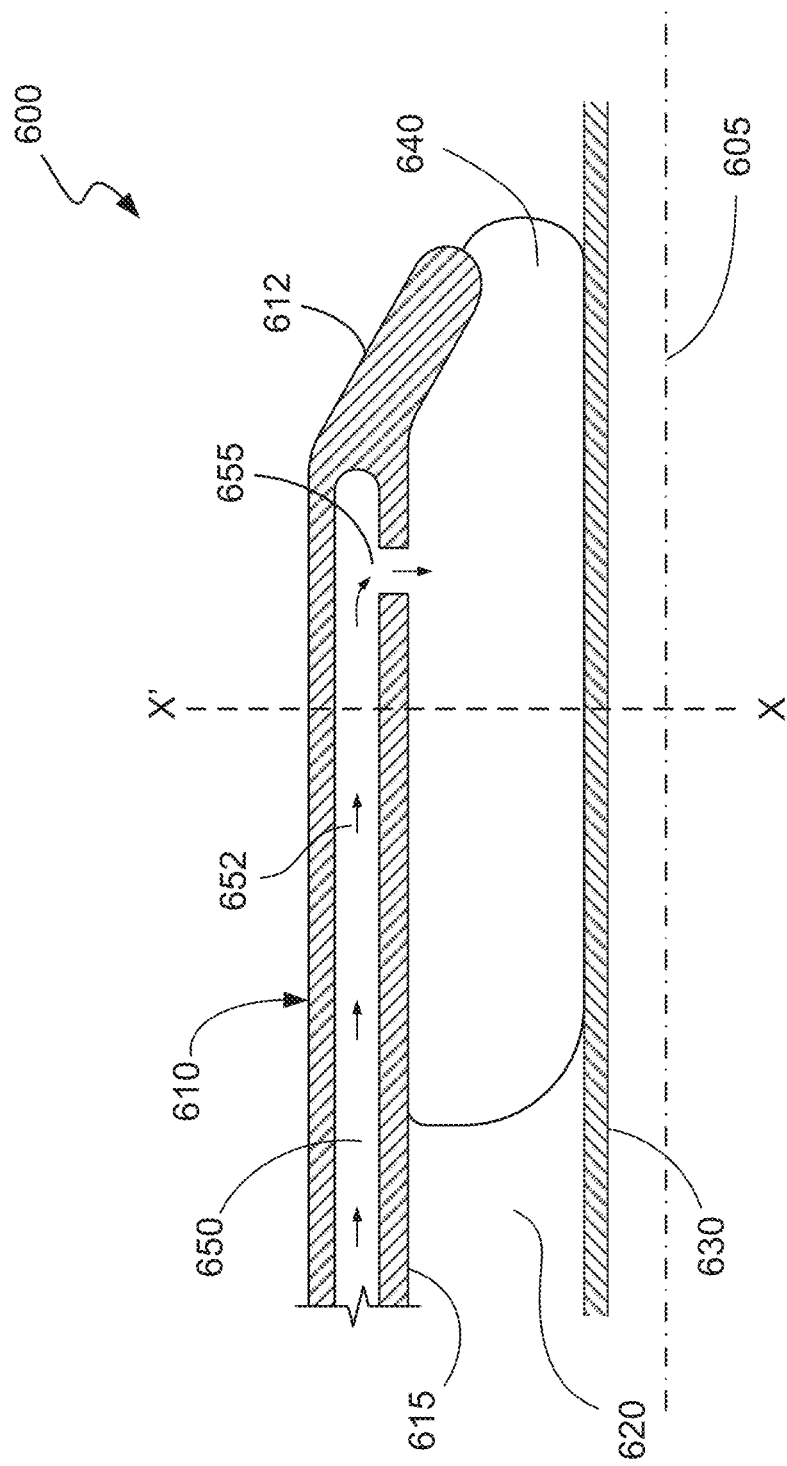
FIG. 6 shows an illustrative inflation lumen and inflation port formed in the sheath body for inflating an internal balloon, according to an embodiment of the present disclosure.

FIG. 6 illustrates an axial cross section of a distal section of an internal balloon sheath 600 according to an embodiment of the present disclosure. As in the embodiments described in the foregoing, sheath 600 comprises a sheath body 610 having an inner surface 615 which defines a lumen 620 for the passage of an intravascular medical device having a catheter body 630. An inflatable balloon 640 is positioned at the distal end 612 of the sheath body 610. The balloon 640 may be compliant or non-compliant, and may be axially symmetric about the longitudinal axis 605 of the sheath body 610, or asymmetric, the configurations of which have been described in the foregoing.

In some embodiments, in order to inflate distally positioned balloons, such as balloon 640, sheath 600 may also be provided with an inflation lumen 650 within the walls of the sheath body 610. Such an inflation lumen 650 may extend from the distal end 612 of the sheath body 610 along the length of the sheath 600 to the proximal end (not shown). The proximal end of the sheath 600 may be coupled to a hub (similar to that shown in FIGS. 5A and 5B). The inflation lumen 650 is in fluid communication with the interior of the balloon 640 via an opening 655 (or radial lumen 655) formed in the wall of the sheath body 610, at the interface between the balloon 640 and the inner surface 615 of the sheath body 610. In some embodiments, balloon 640 may be attached to the inner surface 615 of the sheath body 610 via a heat or solvent bond, as also described in the foregoing. These bonds are critical to ensure that the balloon 640 does not rupture. In certain embodiments, the sheath body 610 may comprise a plurality of lumens similar to lumen 650 for other purposes, such as, for example, localized irrigation and flushing, or for the passage of a guidewire.

Figure 7:
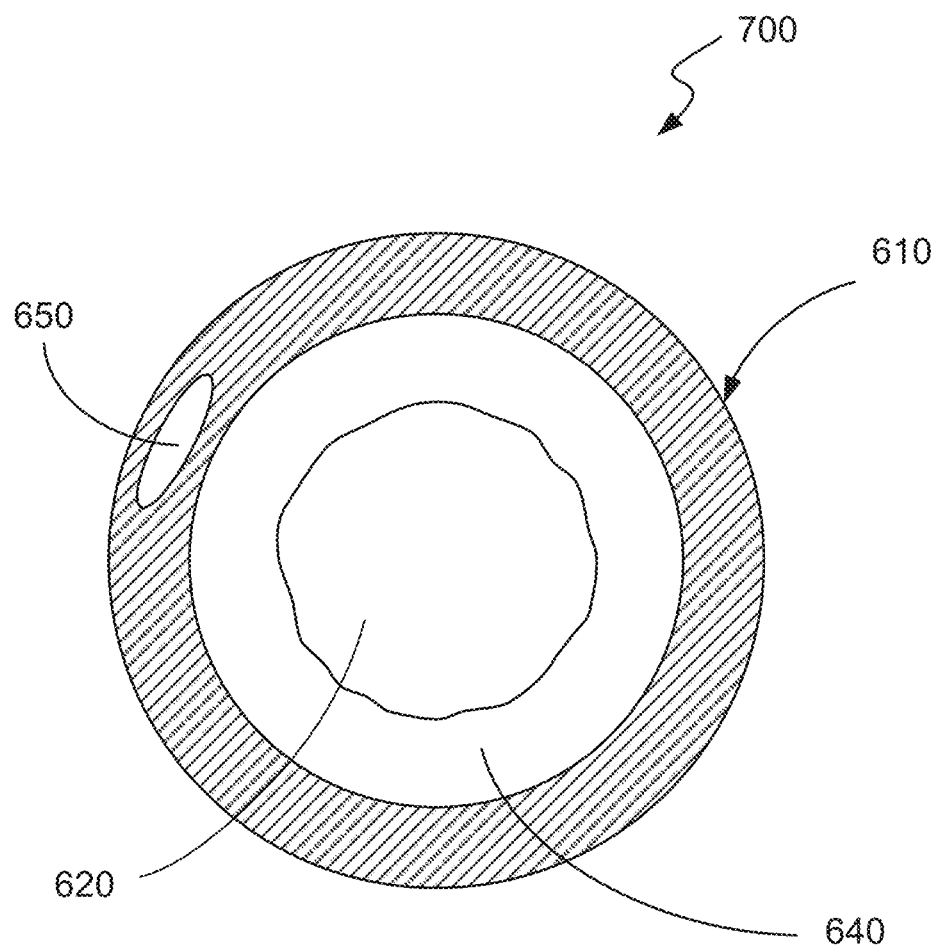
FIG. 7 shows a radial cross section of the internal balloon sheath of FIG. 6.

FIG. 7 shows a cross section 700 of sheath 600 taken about the line X-X' in FIG. 6, showing the inflation lumen 650 formed in the wall of the sheath body 610. In FIG. 7 the balloon 640 is shown as a non-compliant axially symmetric balloon whereby the balloon material resides in the lumen 620 of the sheath body 610 when in the deflated state. However, as mentioned in the foregoing, any type of balloon (compliant, non-compliant, axially symmetric, asymmetric) may be used in conjunction with the embodiments of the present disclosure.

Inflation fluid is provided to the inflation lumen 650 at the hub from a syringe, for example, which then forces the fluid 652 into the inflation lumen 650, through the opening 655 and into the balloon 640 to inflate it. According to embodiments of the present disclosure, inflation fluids may comprise any biocompatible fluid such as, but not limited to, air, water and saline, for example. As mentioned in the foregoing, when the balloon 640 is inflated, it reduces the diameter of the lumen 620 such that the opening in the sheath body 610 is less than the diameter of the catheter body 630 of the medical device. As the balloon is inflated it fills the space between the catheter body 630 and inner surface 615 of the sheath 600 thereby preventing blood ingress, stagnation, and clotting. Once fully inflated, the balloon 640 comes into contact with the catheter body 630 of the medical device and exerts a compressive force on the catheter body 630. Frictional forces between the balloon 640 and the catheter body 630 along the length of the catheter-balloon interface may also assist in the fixation of the position of the catheter body 630 relative to the sheath 600. In some embodiments (when the balloon is not attached to the inner surface of the sheath, as will be described below, for example), frictional forces between the balloon 640 and the inner surface 615 of the sheath body 610 along the balloon-sheath interface also assist in fixating the location of the catheter body 630 relative to the sheath 600.

Figure 8:
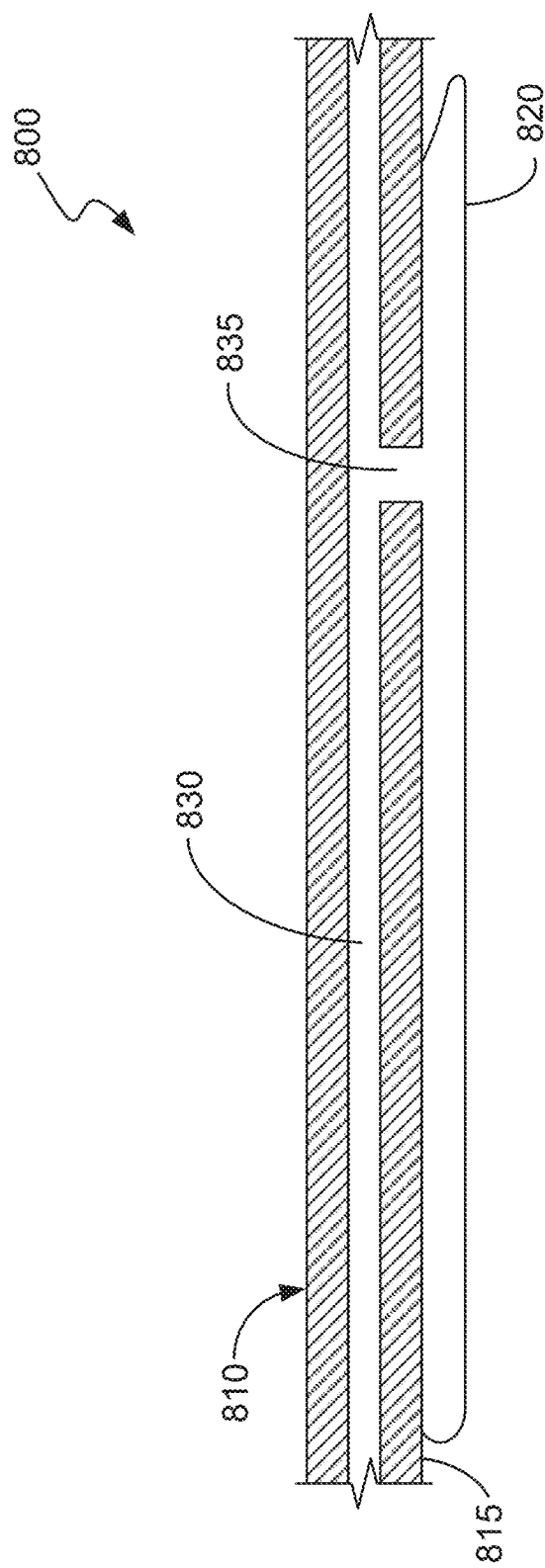
FIG. 8 shows the internal balloon sheath of FIG. 6 prior to inflation.

FIG. 8 illustrates an axial cross section of a section of an internal balloon sheath 800 according to an embodiment of the present disclosure. Sheath 800 comprises similar features to sheath 600 in FIG. 6, however the balloon 820 in sheath 800 is positioned along the sheath body 810 and not at the distal end as in FIG. 6. In FIG. 8 the balloon 820 is shown as non-compliant (and in the deflated state), however it will be understood that the balloon 820 may be configured in any manner as described in the foregoing. Balloon 820 is attached to the inner surface 815 of the sheath body 810 with a heat or solvent bond at locations distal and proximal to the opening 835. As described in relation to sheath 600, opening 835 fluidically connects the inflation lumen 830 to the balloon 820 for the inflation thereof. These bonds are critical to ensure the balloon does not rupture. It will be understood that the configuration depicted in the cross-section of FIG. 8 may vary depending at least on (i) where the balloon 820 is located along the length of the sheath body 810, (ii) how the ends of the balloon 820 are affixed to the inner walls of the sheath body 810, and (iii) the location of the opening 835 relative to the length of the balloon 820. In certain embodiments in which the balloon spans the entire length of the sheath body, the balloon may be inflated directly from the hub without the need for an inflation lumen in the sheath body.

In some embodiments, the inflation lumens as described in with respect to FIGS. 6-8 may be formed in the sheath body by using a mandrel during lamination and reflow of the sheath body. The mandrel does not melt into the layers comprising the sheath body 610, and so can be extracted after reflow thereby leaving the inflation lumen for the passage of inflation fluid to the balloon. The opening that fluidically connects the inflation lumen to the balloon may be formed using a similar process whereby a radially oriented mandrel is positioned in the sheath body before reflow, and subsequently removed. Alternatively, the opening can be punched out of the sheath body after the inflation lumen is formed. Notwithstanding, it will be appreciated that the formation of the inflation lumen and opening may involve complex processing due to the dimensions and tolerances involved.

FIGS. 9A-9B illustrate an exemplary internal balloon sheath 900 according to an embodiment of the present disclosure. Internal balloon sheath 900 comprises a balloon sleeve 910 and an access sheath 920, the balloon sleeve 910 comprising an in-line sleeve that is insertable into the lumen of the access sheath 920. Internal balloon sheath 900 is configured for the passage of a catheter based medical device 930 therethrough. The balloon sleeve 910 comprises a sleeve body 912 with a lumen 911 running therethrough. The distal end of the balloon sleeve 910 may comprise an inflatable balloon 915. Balloon 915 may be attached to the external surface of the distal end of the balloon sleeve 910 using any the attachment means as described in the foregoing. Any type of balloon (compliant, non-compliant, axially symmetric, asymmetric, as described in the foregoing) may be used in conjunction with the embodiments of the present disclosure.

The proximal end of the balloon sleeve 910 may comprise a valve 913 that seals the lumen 911 of the balloon sleeve 910 against the ingress of external fluids. In some embodiments the valve 913 may comprise a haemostatic valve, for example. The proximal end of the balloon sleeve 910 may also comprise a side port 914 that is in fluid communication with the lumen 911 and/or the balloon 915. In certain embodiments, the side port 914 may be in fluid communication with the balloon 915 via an inflation lumen formed in the sleeve body 912, such as inflation lumen 650 shown in FIG. 6. Side port 914 is similar to side ports 525, 530 as discussed in the foregoing with respect to FIG. 5A. In some embodiments, a plurality of side ports may be present on the balloon sleeve 910. Additionally, in certain embodiments, the proximal end of the side port 914 may be coupled to a connector 916 to prevent the backflow of fluid, such as, for example, a Tuohy-Borst adaptor.

In some embodiments, the balloon sleeve 910 may be axially aligned with the catheter 930 of the medical device such that the sleeve 910 is in-line with the catheter 930. In this configuration, the balloon sleeve 910 is co-axially arranged around the catheter 930 of the medical device, as depicted in FIG. 9A. The balloon sleeve 910 may be tightly fit around the catheter 930, while allowing the sleeve 910 to be moved or translated along the catheter 930 into the access sheath 920. In certain embodiments, the catheter 930 of the medical device may be pre-threaded through the lumen 911 of the balloon sleeve prior to use. In some embodiments, the catheter of the medical device may be manufactured with the balloon sleeve 910 coaxially arranged around the catheter 930.

The access sheath 920 is similar to the sheaths that have been described in the foregoing in relation to FIGS. 4-8. Access sheath 920 comprises a sheath body 922 having a proximal end 924, a distal end 926 and a lumen 928 running between the proximal and distal ends. The proximal end 924 may be coupled to a hub 940. Hub 940 is similar to hub 520 depicted in FIG. 5A, and may have at least one side port 942 positioned thereon. The side port 942 may be in fluid communication with the lumen 928 of the access sheath 920 for irrigation and flushing, for example.

As previously described, the distal end of intravascular medical devices usually has the largest diameter compared to the catheter body. The sheath body 922 is configured such that the diameter of the lumen 928 is large enough to allow the distal end of the medical device to pass through the lumen 928. Additionally, the lumen 928 may be configured such that it allows the balloon sleeve 910 to pass therethrough, i.e. the lumen 928 has a diameter that is larger than the external diameter of the balloon sleeve 910. In certain embodiments of the present disclosure, the diameter of the lumen 928 is such that a space 950 develops between the external surface of the balloon sleeve body 912 and the internal surface of the sheath body 922 when the balloon sleeve 910 is inserted into the lumen 928 of the access sheath 920. This space is similar to that as described in the foregoing in relation to FIG. 4. In some embodiments, the axial length of the balloon sleeve 910 may be larger than the axial length of the access sleeve 920. This ensures that at least a portion of the proximal end of the balloon sleeve 910 sticks out of the hub 940 of the access sheath 920 when the balloon sleeve 910 is inserted into the access sheath 920. This allows for the proximal end of the balloon sleeve 910 (and the side ports attached thereto) to be easily accessed, for inflation of the balloon 915, or example.

FIG. 9B shows the cross section of the internal balloon sheath 900 once the balloon sleeve 910 is moved along the catheter 930 of the medical device and into the lumen 928 of the access sheath 920. The balloon sleeve 910 would be positioned within the access sheath 920 after the lumen 928 is flushed with an irrigation fluid (e.g. saline or water) via side port 942. In FIG. 9B, the balloon 915 is shown as being in the inflated state. The balloon 915 may be inflated with an inflation fluid provided via side port 942. While not shown in FIG. 9A, this may be via an inflation lumen formed within the balloon sleeve body 912. As mentioned in the foregoing, when the balloon 915 is inflated, the balloon material may be elastically deformed by the pressure from the inflating fluid (which, in turn, may be delivered to the balloon 915 via a syringe, for example) causing it to seal against the catheter body 930, thereby closing off the lumen to entrants from the arteriotomy (such as, for example, blood and clots). When the balloon 915 is inflated, it exerts a radially expansive force on the inner surface of the access sheath body 922 from all directions, thereby effectively fixing the position of the balloon sleeve 910 relative to the access sheath 920. In some embodiments, the access sheath 920 may be made of a material that deforms under the influence of such compressive forces, as will be described in relation to FIG. 13 in the following section. Additionally, when the balloon 915 is inflated, it also exerts a radially compressive force on the catheter body 930 from all directions about the catheter, thereby effectively gripping the catheter body 930 and locking it in position.

Figure 10A:
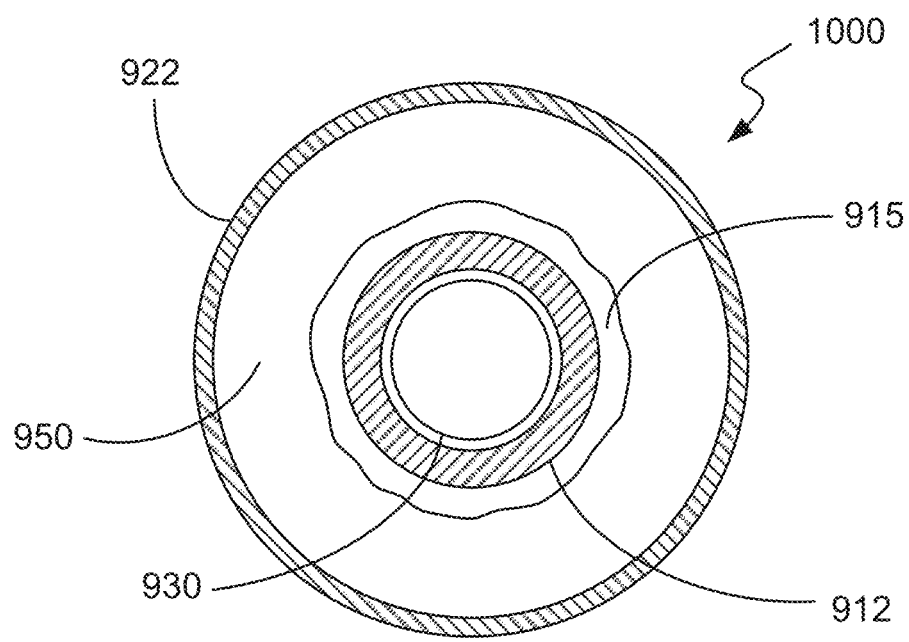
FIG. 10A shows a radial cross section of the internal balloon sheath of FIGS. 9A-9B prior to inflation.

FIG. 10A shows a cross section 1000 of the in-line internal balloon sheath 900 taken about the line Y-Y' in FIG. 9B before balloon 915 is inflated. FIG. 10A shows the balloon sleeve 910 coaxially arranged around the catheter body 930 of the medical device. As mentioned, the balloon sleeve 910 is tightly fit around the catheter body 930 while being slidable on the catheter body 930. The balloon sleeve 910 is inserted into the lumen 928 of the access sheath 920. As previously described, in some embodiments, the balloon sleeve 910 may comprise an inflation lumen that fluidically connects an inflation port 914 on the proximal end of the balloon sleeve 910 to the balloon 915 for inflation of the balloon. FIG. 10A shows the space 950 between the external surface of the balloon sleeve body 912 and the internal surface of the sheath body 922 when the balloon sleeve 910 is inserted into the lumen 928 of the access sheath 920. While the balloon 915 is illustrated as being coaxially arranged with the balloon sleeve 910, any orientation of the balloon 915 with respect to the balloon sleeve body 912 may be used. For example, the balloon 915 may be positioned on at least one portion of the external surface of the balloon sleeve body 912.

Figure 10B:
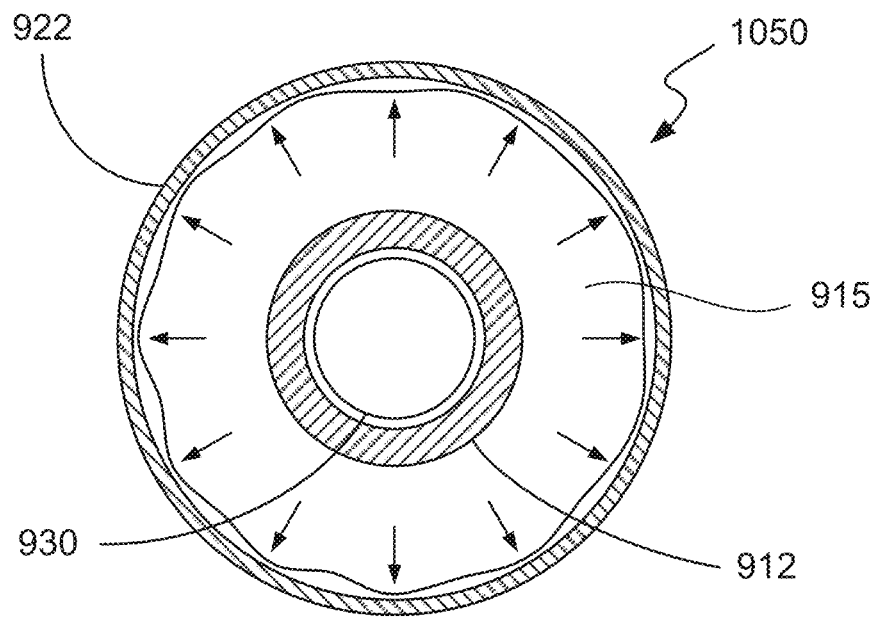
FIG. 10B shows a radial cross section of the internal balloon sheath of FIGS. 9A-9B after inflation.

FIG. 10B shows a cross section 1050 of the in-line internal balloon sheath 900 taken about the line Y-Y' in FIG. 9B after balloon 915 is inflated. When the balloon 915 is inflated, the balloon material may elastically deform by the pressure from the inflating fluid (which, in turn, may be delivered to the balloon 915 via a syringe, for example) causing it to seal against the inner surface of the access sheath 920. As can be seen, the balloon 915 occupies the space 950 upon inflation, thereby preventing fluid ingress (such as, for example, blood and clots) into the lumen 928 of the access sheath 920. It will be understood throughout this disclosure that 'seal' is to be taken to mean substantially sealing of a lumen so as to eliminate fluid flow of any amount that would enable formation of clots. When the balloon 915 is inflated, it exerts a radially expansive force on the inner surface of the access sheath body 922 from all directions, thereby effectively fixing the position of the balloon sleeve 910 relative to the access sheath 920. In some embodiments, the access sheath 920 may be made of a material that deforms under the influence of such compressive forces, as will be described in relation to FIG. 13 in the following section. Additionally, when the balloon 915 is inflated, it also exerts a radially compressive force on the catheter body 930 from all directions about the catheter, thereby effectively gripping the catheter body 930 and locking it in position.

Figure 11A:
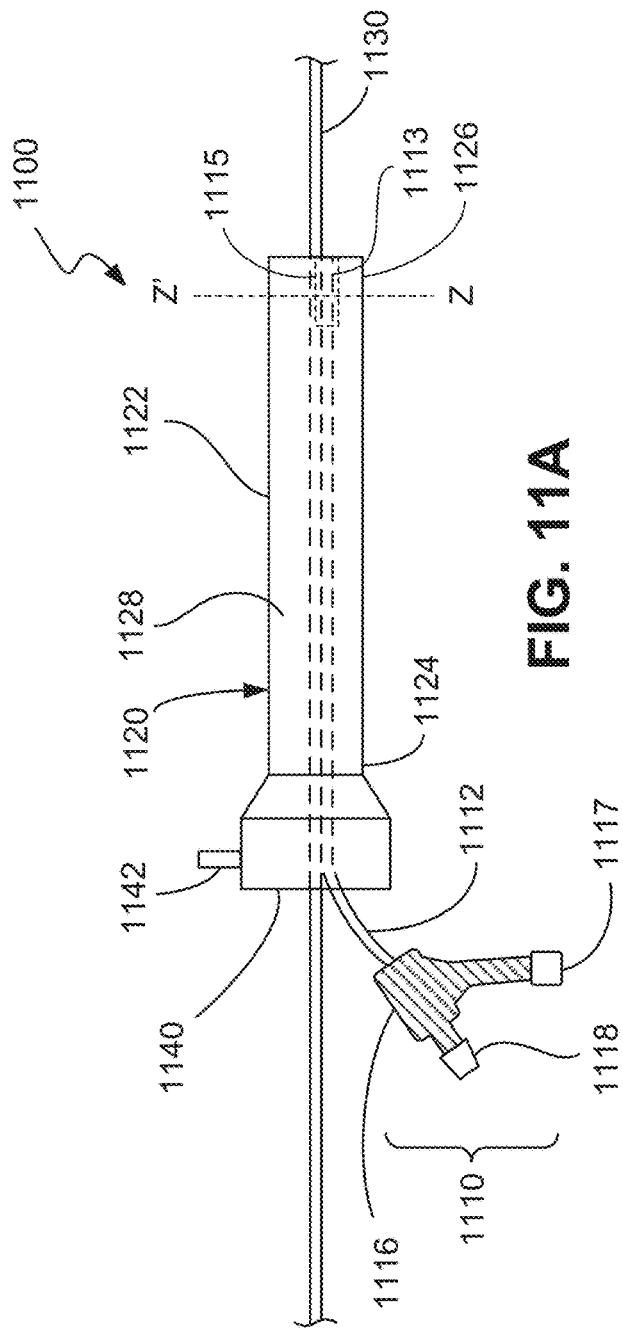
FIG. 11A shows an illustrative internal balloon sheath with a non-inline balloon sleeve according to an embodiment of the present disclosure.
Figure 11B:
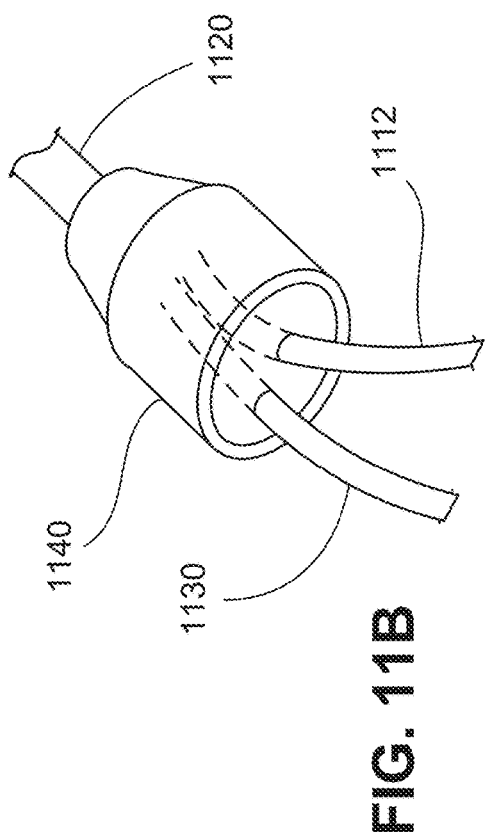
FIG. 11B shows an isometric view of the proximal end of the internal balloon sheath of FIG. 11A.

FIGS. 11A-11B illustrate an exemplary internal balloon sheath 1100 according to an embodiment of the present disclosure. Internal balloon sheath 1100 comprises a balloon sleeve 1110 and an access sheath 1120. Unlike the balloon sleeve 910 in FIGS. 9A-9B, the balloon sleeve 1110 shown in FIGS. 11A-11B is not positioned in-line with the catheter of a medical device. Balloon sleeve 1110 comprises a sleeve body 1112 having a balloon 1115 located at the distal end 1113 thereof. In some embodiments, the balloon 1115 may be located at any point along the sleeve body 1112. The sleeve body 1112 may have a central lumen that is fluidically connected to the balloon 1115 for inflation. The balloon 1115 may be oriented in any manner with respect to the balloon sleeve body 1112 may be used. For example, the balloon 1115 may be symmetrically arranged about the sleeve body 1112, or the balloon 1115 may be asymmetrically arranged about the sleeve body 1112. Further, balloon 1115 may be attached to the external surface of the distal end 1113 of the sleeve body 1112 using any of the attachment means as described in the foregoing. Any type of balloon (compliant, non-compliant, axially symmetric, asymmetric, as described in the foregoing) may be used in conjunction with the embodiments of the present disclosure.

The proximal end of the balloon sleeve 1110 may be coupled to a sleeve hub 1116, which, in turn, may be provided with at least one side port 1117. The side port 1117 may be in fluid communication with the central lumen in the sleeve body 1112 and/or the balloon 1115. As described in the foregoing, the side port may be used as an inflation port to inflate the balloon 1115 with an inflation fluid after the sheath 1100 is positioned in the arteriotomy of the patient. Hub 1116 may also be provided with a connector port 1118 for the coupling of an additional adaptor to prevent the backflow of fluid, such as, for example a Tuohy-Borst adaptor.

Access sheath 1120 is similar to access sheath 920 in FIG. 9A as described in the foregoing. Access sheath 1120 comprises a sheath body 1122 having a proximal end 1124, a distal end 1126 and a lumen 1128 running between the proximal and distal ends. The proximal end 1124 may be coupled to a hub 1140. Hub 1140 is similar to hub 520 depicted in FIG. 5A, and may have at least one side port 1142 positioned thereon. The side port 1142 may be in fluid communication with the lumen 1128 of the access sheath 1120 for irrigation and flushing the lumen 1128, for example.

The sheath body 1122 is configured such that the diameter of the lumen 1128 is large enough to allow the distal end of the medical device to pass through. Additionally, the lumen 1128 is configured such that it allows both the balloon sleeve 1110 and the catheter body 1130 of the medical device to pass therethrough, i.e. the lumen 1128 has a diameter that is larger than the combined external diameters of both the sleeve body 1112 and the catheter body 1130. In certain embodiments of the present disclosure, the diameter of the lumen 1128 is such that a space 1150 develops between the external surface of the balloon sleeve body 1112, the external surface of the catheter body 1130, and the internal surface of the sheath body 1122 when the catheter 1130 of the medical device and the balloon sleeve 1110 are both inserted into the lumen 1128 of the access sheath 1120 (see FIG. 12A, described below). This space is similar to that as described in the foregoing in relation to FIG. 4.

In some embodiments, the axial length of the balloon sleeve 1110 may be larger than the axial length of the access sleeve 1120. This ensures that at least a portion of the proximal end of the balloon sleeve 1110 sticks out of the hub 1140 of the access sheath 1120 when the balloon sleeve 1110 is inserted into the access sheath 1120, as shown in FIG. 11B. This allows for the proximal end of the balloon sleeve 1110 (and the side ports attached thereto) to be easily accessed, for inflation of the balloon 1115, or example.

Figure 12A:
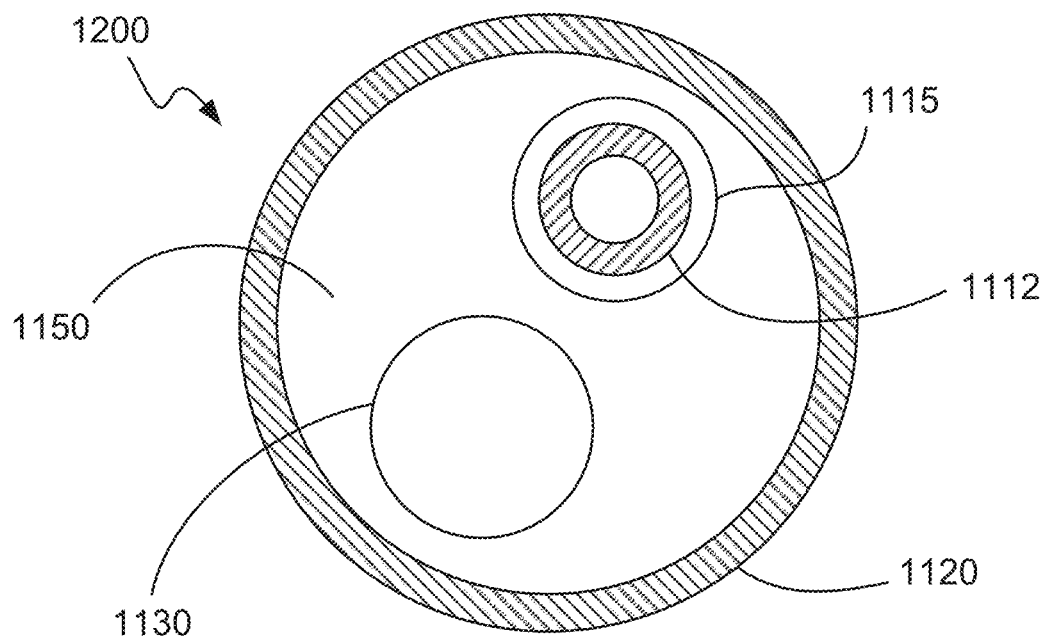
FIG. 12A shows a radial cross section of the internal balloon sheath of FIGS. 11A-11B prior to inflation.

FIG. 12A shows a cross section 1200 of the internal balloon sheath 1100 taken about the line Z-Z' in FIG. 11B before balloon 1115 is inflated. The balloon sleeve 1110 is inserted into the lumen 1128 of the access sheath 1120, and comprises a sleeve body 1112 having an inflation lumen formed therethrough, the lumen being in fluid communication with the balloon 1115. In some embodiments, the balloon sleeve body 1112 may comprise an inflation lumen that fluidically connects the inflation port 1117 on the proximal end of the balloon sleeve 1112 to the balloon 1115 for inflation of the balloon. FIG. 12A shows the space 1150 between the internal surface of the sheath body 1122, the external surface of the catheter body 1130 and the external surface of the balloon sleeve 1110, after the medical device and the balloon sleeve 1110 have been inserted into the lumen 1128 of the access sheath 1120. While the balloon 1115 is illustrated as being concentrically arranged around the balloon sleeve body 1112, any orientation of the balloon 1115 with respect to the balloon sleeve body 1112 may be used. For example, the balloon 1115 may be positioned on at least one portion of the external surface of the balloon sleeve body 1112.

Figure 12B:
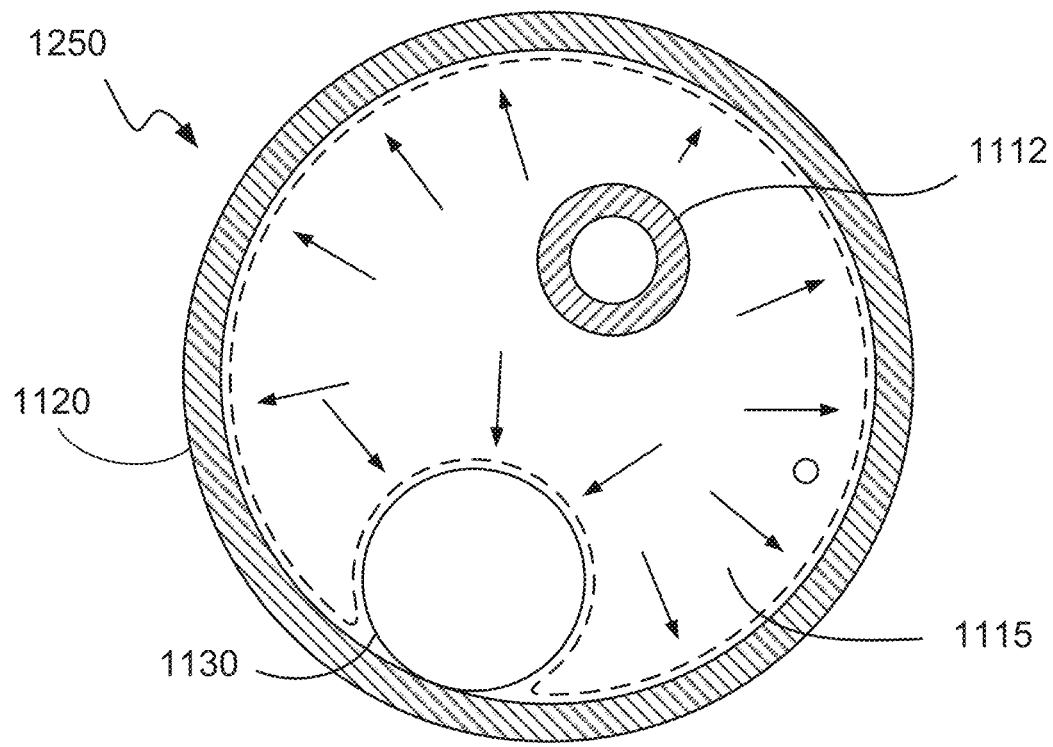
FIG. 12B shows a radial cross section of the internal balloon sheath of FIGS. 11A-11B after inflation.

FIG. 12B shows a cross section 1250 of the internal balloon sheath 1100 taken about the line Z-Z' in FIG. 11A after balloon 1115 is inflated. When the balloon 1115 is inflated, the balloon material may elastically deform by the pressure from the inflating fluid (which, in turn, may be delivered to the balloon 1115 via a syringe, for example) causing it to seal against the catheter body 1130. As can be seen, the balloon 1115 occupies the space 1150 upon inflation, thereby preventing fluid ingress (such as, for example, blood and clots) into the lumen 1128 of the access sheath 1120. It will be understood throughout this disclosure that 'seal' is to be taken to mean substantially sealing of a lumen so as to eliminate fluid flow of any amount that would enable formation of clots. When the balloon 1115 is inflated, it exerts a radially expansive force on the inner surface of the access sheath body 1122 from all directions, thereby effectively fixing the position of the balloon sleeve 1110 relative to the access sheath 1120. Additionally, when the balloon 1115 is inflated, it exerts a radially compressive force on the catheter body 1130 so as to pin the catheter body 1130 of the medical device against the inner surface of the access sheath 1120, thereby effectively gripping the catheter body 1130 and locking it in position. In some embodiments, the access sheath 1120 may be made of a material that deforms under the influence of such expansive forces, as will be described in relation to FIG. 13 in the following section.

Figure 13:
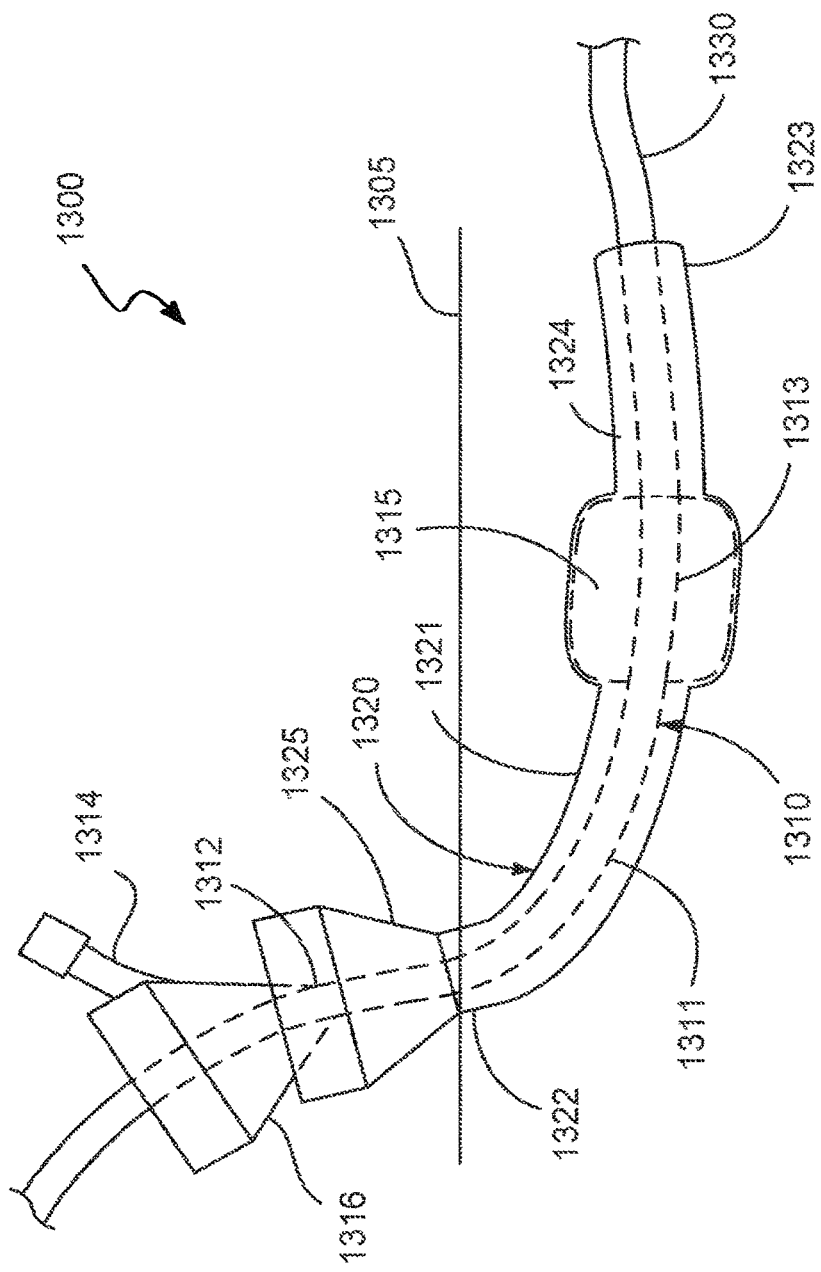
FIG. 13 shows an illustrative expandable internal balloon sheath with an inline balloon sleeve according to an embodiment of the present disclosure where the balloon and sheath are specifically designed to allow for local expansion of the sheath.

FIG. 13 illustrates an exemplary internal balloon sheath 1300 according to an embodiment of the present disclosure. Internal balloon sheath 1300 comprises an inflatable balloon sleeve 1310 and an access sheath 1320. Balloon sleeve 1310 may be similar to balloon sleeves 910, 1110 as described in the foregoing with respect to FIGS. 9-12. Sleeve 1310 comprises a sleeve body 1311 having a proximal end 1312 and a distal end 1313. An inflatable balloon 1315 may be attached to the distal end 1313 of the outer surface of the sleeve body 1311. The proximal end 1312 may be coupled to a hub 1316, which, in turn, may be provided with an inflation port 1314. Inflation port 1314 is configured to be in fluid communication with the balloon 1315 such that inflation fluid input at the inflation port 1314 inflates the balloon 1315. In some embodiments, the inflation port 1314 may be fluidically connected to the balloon 1315 via an inflation lumen formed in the walls of the sleeve body 1311.

The balloon 1315 may be oriented in any manner with respect to the balloon sleeve body 1311. For example, the balloon 1315 may be symmetrically arranged about the sleeve body 1311, or the balloon 1315 may be asymmetrically arranged about the sleeve body 1311. Further, balloon 1315 may be attached to the external surface of the distal end 1313 of the balloon sleeve 1310 using any of the attachment means as described in the foregoing. Any type of balloon (compliant, non-compliant, axially symmetric, asymmetric, as described in the foregoing) may be used in conjunction with the embodiments of the present disclosure.

As with the balloon sleeve 1310, access sheath 1320 may be similar to access sheaths 920, 1120 as described in the foregoing with respect to FIGS. 9-12. Access sheath 1320 comprises a sheath body 1321 having a proximal end 1322, a distal end 1323 and a lumen 1324 running between the proximal and distal ends. The proximal end 1322 may be coupled to a hub 1325. Hub 1325 may have at least one side port (not shown) positioned thereon which may be in fluid communication with the lumen 1324 of the access sheath 1320 for irrigation and flushing the lumen, for example.

The sheath body 1321 is dimensioned such that the diameter of the lumen 1324 is large enough to allow a distal end of the medical device to pass through. Additionally, the lumen 1324 is configured such that it allows the balloon sleeve 1310 to pass through. In certain embodiments of the present disclosure, the diameter of the lumen 1324 is such that a space develops between the external surface of the balloon sleeve body 1311 and the internal surface of the sheath body 1321 when the balloon sleeve body 1311 (positioned in-line with the catheter 1330 of the medical device) is inserted into the lumen 1324 of the access sheath 1320. While FIG. 13 depicts the balloon sleeve 1310 to be in-line with the catheter 1330 of the medical device (such as in FIGS. 8-9), the balloon sleeve 1310 may, alternatively, be adjacent the catheter 1330 of the medical device (such as in FIGS. 10-11).

As described in the foregoing embodiments, when the balloon 1315 is inflated with fluid, the balloon occupies the aforementioned space between the external surface of the balloon sleeve body 1311 and the internal surface of the sheath body 1321, thereby sealing the lumen 1324 from ingress of blood from the arteriotomy of the patient. In the embodiment depicted in FIG. 13, the sheath body 1321 is capable of elastic deformation such that when the balloon 1315 expands in size, the expansive force from the inflating balloon 1315 also causes the sheath body 1321 adjacent the balloon to deform. This causes bulging in the access sheath 1320 which prevents axial movement of the internal balloon sheath 1300 after insertion into the patient. Thus, in addition to sutures or tape that fixes the location of the hub 1325 to the skin 1305 of the patient, the bulge in the access sheath 1320 when the balloon 1315 is inflated locks the position of the sheath 1300 thereby further securing the sheath 1300 to the patient.

In all the embodiments described in the foregoing, the sheath may comprise a rigid material. The rigid material may be a polyethylene (PE) or polyurethane (PU) material. In certain embodiments, the rigid material may have an elastic modulus of about 40 ksi (285 MPa). Ksi is a unit of pressure, representing thousands of pounds per square inch. In some embodiments the rigid material contains a radiopaque filler such as bismuth oxychloride or barium sulfate in concentrations of 5% to 40% by weight. In some embodiments, the rigid material may be any one of a polyether block amide (such as PEBAX or PebaSlix®), a polyethylene material, a polytetrafluoroethylene (PTFE) material, a high-density polyethylene (HDPE) material, a medium-density polyethylene (MDPE) material, a low-density polyethylene (LDPE) material, polyether ether ketone (PEEK), a polyether block amide (such as PEBAX) and nylon. In certain implementations, the rigid material is a crack-resistant material. In some embodiments, the rigid material may also be a material with a low coefficient of friction. Additionally, in all the embodiments described in the foregoing, the hub may also comprise any one of the above rigid materials. Generally the strength of the sheath is dependent on the modulus of the rigid material as well as the thickness of the sheath wall. For rigid materials having a lower elastic modulus, the resulting sheath will require a wall of greater thickness. Conversely, rigid materials having a higher modulus allows for a sheath having a lower wall thickness.

In all the embodiments described in the foregoing, the sheath body may comprise a coaxially layered structure as described in U.S. Provisional Patent Application No. 62/777,598, the contents of which are hereby incorporated by reference in entirety. Each layer of the structure may comprise a different polymer. The layering of the polymers improves the strength of the sheath while maintaining flexibility, which is ideal for application to intravascular applications as detailed in the present disclosure. The polymers may comprise any one of PEBAX® 7233SA, PEBAX® 7033SA, PEBAX® 6333SA, PEBAX® 5533SA, PEBAX® 3533SA, and PEBAX® 2533SA. In other embodiments, the sheath may comprise various sections that are sequentially arranged, each section comprising a different polymer. Such an arrangement provides for a varying mechanical strength along the length of the sheath body. The polymers may comprise any of the aforementioned rigid materials. In certain embodiments, the sheath body may be reinforced with braids or coils to improve mechanical strength, these structures being constructed from wires made from any one of the aforementioned rigid materials. In some embodiments, the structure of the sheath body may be strengthened by laser cutting the tubular sheath body with features that enhance its strength.

Further, in all the embodiments described in the foregoing, the balloon may comprise a flexible material. The flexible material may comprise a polyethylene or polyurethane material with an elastic modulus of about 40 ksi. In some embodiments the material may be any one of urethane, polyurethane, polyethylene, polypropylene, polyethylene terephthalate (PET), polyvinyl chloride (PVC), polyethylene, cross-linked polyethylene, a polyether block amide (PEBA), and nylon. In some embodiments, the balloon sleeve may also comprise a flexible material as defined in the foregoing.

Additionally, in all the embodiments described in the foregoing, the hub may comprise a rigid material. The rigid material may be a polyethylene or polyurethane material with an elastic modulus of about 40 ksi. In some implementations, the rigid material is any one of a high-density polyethylene (HDPE) material, a medium-density polyethylene (MDPE) material, a low-density polyethylene (LDPE) material, polyether ether ketone (PEEK), and a polyether block amide (such as PEBAX). In certain implementations, the rigid material is a crack-resistant material. In some implementations, the rigid material may also be a material with a low coefficient of friction.

In all the embodiments described in the foregoing, a coating may be applied to the balloon so as to reduce the friction during passage of interventional devices through the internal balloon sheath. In certain embodiments, the coating may be hydrophilic or hydrophobic. In some embodiments, the thickness of this coating may be varied to achieve desired inflation characteristics of the balloon. Additionally, in all the embodiments described in the foregoing, the inner surface of the sheath may be pretreated to improve the likelihood of bonding with the balloon. Such pretreatment may include, but is not limited to, plasma activation or coronary treatment. Alternatively, or in addition to the aforementioned coatings, a coating may be applied to the catheter based medical device itself prior to insertion into the internal balloon sheath.

Additionally, in all the embodiments described in the foregoing, the sheath body may additionally comprise a distal tip made up of a softer material than that used for the sheath body, i.e. the distal tip may comprise a material that has a lower elastic modulus than that of the material used for the sheath body. In some embodiments, the distal tip may be beveled to aid with insertion of the sheath into the arteriotomy of the patient. Such distal tips can seal down on catheters of smaller diameters. By sealing on the catheter, blood is prevented from entering the sheath body and clot. In certain embodiments the distal tip may contain a radiopaque filler such as bismuth oxychloride or barium sulfate in concentrations of 5% to 40% by weight.

Figure 14:
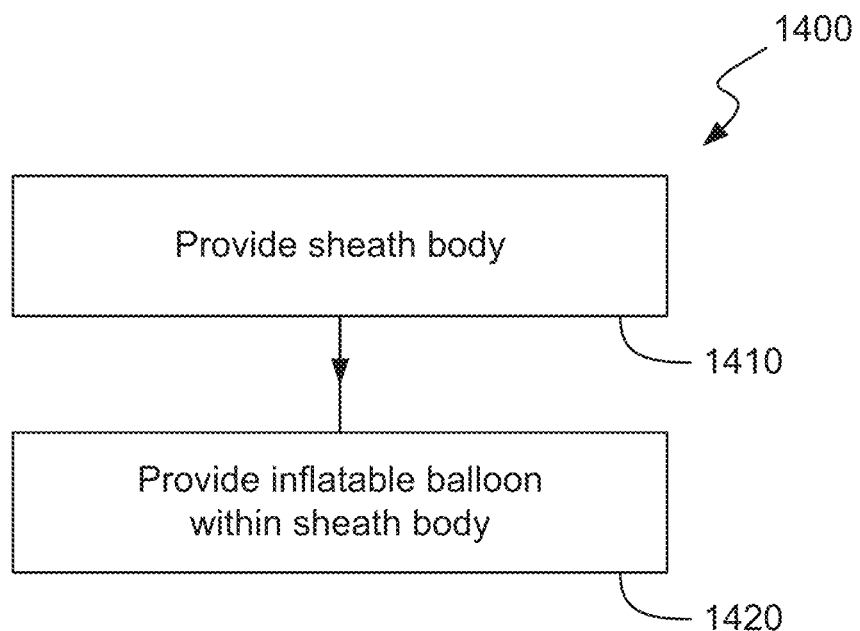
FIG. 14 shows an illustrative flowchart of a method of fabricating an internal balloon sheath according to an embodiment of the present disclosure.

FIG. 14 illustrates an exemplary method 1400 of fabricating an internal balloon sheath, such as any of the balloon sheaths as described in the foregoing description, according to an embodiment of the present disclosure. The method 1400 begins at step 1410 in which a sheath body is made available for fabrication. The sheath body may be provided by extrusion of lamination. As described in the foregoing, the sheath body having a longitudinal axis and comprising an open proximal end, an open distal end, an outer surface and an inner surface, the inner surface defining a lumen between the proximal and distal ends. In some embodiments, the method may include the fabrication of a tubular sheath. In certain embodiments, the method may comprise the fabrication of a sheath with a diameter that is larger than the external diameter of a distal end of catheter based intravascular medical device, such as, for example, a heart pump, so as to allow the passage of the medical through the lumen of the sheath body.

In certain embodiments, the method may include the fabrication of a sheath body that may comprise a coaxially laminated layered structure. Further, in some embodiments, the sheath body may comprise structural reinforcements such as a coil or braid. Such layered and/or reinforced body structures enable the sheath to withstand larger pushing forces, such as those experienced during the positioning of the internal balloon sheath in the arteriotomy of the patient. In some embodiments, the structure of the sheath body may be strengthened by laser cutting the tubular sheath body with features that enhance its strength. In certain embodiments, the inner surface of the sheath body may be pretreated (via plasma activation or coronary treatment, for example) to improve the likelihood of bonding with a balloon.

The method then continues to step 1420, in which an inflatable balloon is provided within the sheath body. In some embodiments, the balloon is provided by extrusion or blow molding. In certain embodiments, the method comprises attaching the balloon to the inner wall of the sheath body where the balloon is contained within the inner diameter of the sheath body. In some embodiments, the method further comprises attachment of the balloon to a balloon sleeve which is insertable into the lumen of the sheath body. In some embodiments, the method comprises the attachment of a balloon that extends along the entire length of the sheath body. In other embodiments, the method comprises attachment of a balloon that only extends along a portion of the length of the sheath body. In some embodiments, the method comprises the attachment of the balloon at only a portion of the inner surface of the sheath body, such as, for example, the distal end of the sheath body. In other embodiments, the method comprises attachment of the balloon to the inner surface of the sheath body (or the outer surface of the balloon sleeve) along the entire length of the balloon. Further, in some embodiments, the method comprises attachment of the balloon along the entire circumference of the sheath body (or the balloon sleeve). In other embodiments, the method comprises attachment of the balloon along at least a portion of the circumference of the sheath body (or the balloon sleeve).

Additionally, in some embodiments, the method comprises the attachment of a balloon that is in-line with (i.e. radially symmetrical about) the catheter body of a medical device traversing through the lumen of the sheath. In other embodiments, the method comprises the attachment of a balloon that is radially asymmetrical about the catheter body of a medical device traversing through the lumen of the sheath.

Figure 15:
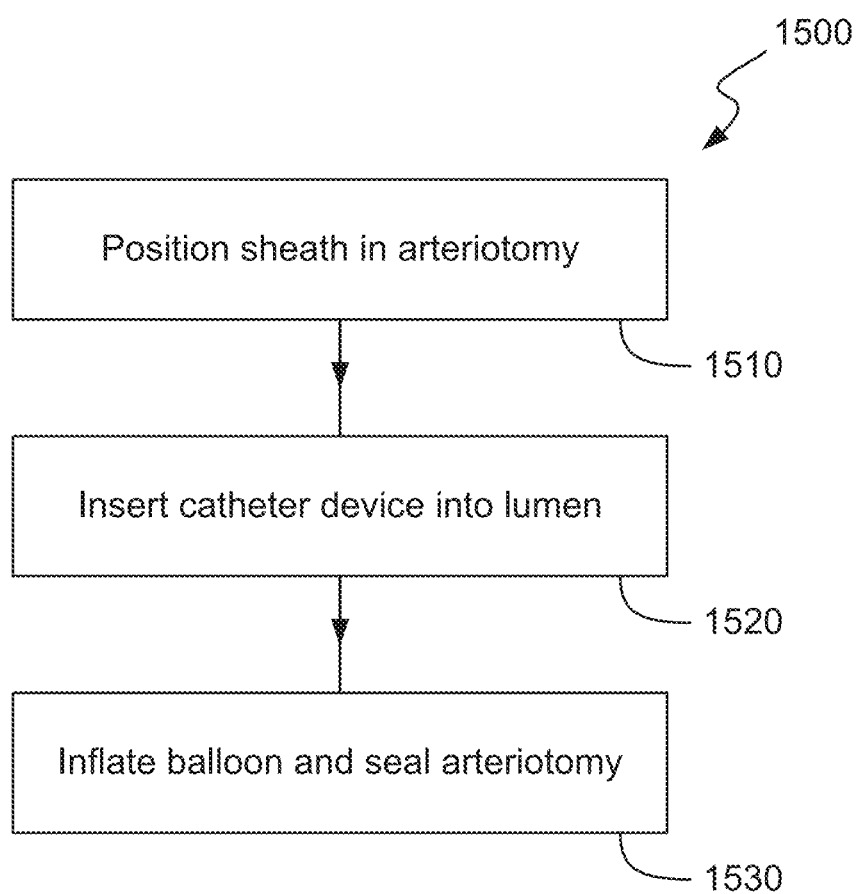
FIG. 15 shows an illustrative flowchart of a method of using an internal balloon sheath according to an embodiment of the present disclosure.

FIG. 15 illustrates an exemplary method 1500 of using an internal balloon sheath, such as any of the balloon sheaths as described in the foregoing description, according to an embodiment of the present disclosure. The method 1500 begins at step 1510 in which an internal balloon sheath is positioned into the arteriotomy of the patient. As previously mentioned, any of the sheaths described in the foregoing may have a tip formed on a patient proximate end of the sheath body. Such a tip may be beveled to aid with insertion into the patient. In some embodiments, the sheath body may have a laminated structure that is able to withstand large pushing forces, such as those used to insert the sheath into the patient, without kinking, bending or buckling. In certain embodiments, a dilator may be inserted into the lumen of the sheath before insertion into the patient. The dilator assists with positioning the sheath in regions of the patient's body which are difficult to penetrate with the sheath alone. Once inserted, the dilator is removed from the lumen of the sheath.

In step 1520, the catheter based medical device is inserted into the lumen of the sheath. The medical device is advanced into the lumen of the sheath body until it emerges from the distal tip of the sheath and is positioned in the arteriotomy of the patient. In some embodiments, the physician may manipulate the position of the medical device by holding onto a hub affixed to the proximal end of the catheter body of the medical device. Once in position, the catheter hub may be coupled to the hub of the sheath located on the exterior surface of the patient.

In some embodiments, the sheath may comprise an internal balloon attached to the internal surface of the sheath body, as described in the foregoing. In other embodiments, the balloon may be located on an additional balloon sleeve that is slidably arranged along the catheter body of the medical device. Once the sheath is in position and the medial device is inserted into the arteriotomy of the patient, the balloon sleeve may be slid into position, along the catheter body. The balloon sleeve is positioned between the internal surface of the sheath body and the external surface of the catheter body. The various configurations and attachments of the internal balloon to the sheath and/or the balloon sleeve that have been described in the foregoing description, while omitted here for brevity, are applicable to the method 1500.

As described in the foregoing, a space may exist between the inner surface of the sheath body and the external surface of the catheter body. In order to prevent stagnation and clotting during positioning of the medical device, the once the medical device is positioned in the arteriotomy of the patient, the method may optionally comprise the flushing of the lumen of the sheath body (and hence the space) with an irrigation fluid, such as, for example, saline or water. Such irrigation fluid may be provided to the lumen via an irrigation side port fluidically connected to the lumen, as described in the foregoing.

In step 1530, a balloon is inflated within the lumen of the sheath with an inflation fluid, thereby fluidically sealing the lumen, and the space between the inner surface of the sheath body and the external surface of the catheter body. It will be understood throughout this disclosure that 'seal' is to be taken to mean substantially sealing of a lumen so as to eliminate fluid flow of any amount that would enable formation of clots. Inflation fluids may include saline, air or water, for example. Such inflation fluid may be provided to the balloon via an inflation side port fluidically connected to the balloon, as described in the foregoing. In some embodiments an inflation lumen may be provided within the sheath body to deliver the inflation fluid to the balloon.

Once the balloon is inflated, the balloon forms an interference fit with the inner surface of the sheath body and the external surface of the catheter body, thereby also preventing any axial movement of the catheter body. As such the balloon effectively locks the medical device in place after the balloon is inflated. In certain embodiments, inflation of the balloon also causes the elastic deformation of the sheath body, whereby the sheath body adjacent the inflated balloon expands into a bulge within the arteriotomy o the patient. Such a bulge will further fix the position of the internal balloon sheath within the vasculature of the patient while the medical device is in use, thereby securing it.

If desired, the different steps discussed herein may be performed in a different order and/or concurrently with each other. Furthermore, if desired, one or more of the above described steps may be optional or may be combined.

The foregoing is merely illustrative of the principles of the disclosure, and the devices and methods can be practiced by other than the described implementations, which are presented for purposes of illustration and not of limitation. It is to be understood that the devices and methods disclosed herein, while shown for use in manufacture of an internal balloon sheath, may be applied to other systems in which sealable sheaths of a single diameter for insertion into the vasculature of the patient are required during intravascular procedures.

Variations and modifications will occur to those of skill in the art after reviewing this disclosure. The disclosed features may be implemented, in any combination and subcombination (including multiple dependent combinations and subcombinations), with one or more other features described herein. The various features described or illustrated above, including any components thereof, may be combined or integrated in other systems. Moreover, certain features may be omitted or not implemented.

Examples of changes, substitutions, and alterations are ascertainable by one skilled in the art and could be made without departing from the scope of the information disclosed herein. All references cited herein are incorporated by reference in their entirety and made part of this application.

ILLUSTRATIVE EMBODIMENTS

A1. A sheath for delivery of a catheter device through an arteriotomy of a patient, the sheath comprising:
a tubular sheath body having a longitudinal axis, an open proximal end, an open distal end, an outer surface and an inner surface, the inner surface defining a lumen between the proximal and distal ends for passage of a catheter device; and
an inflatable balloon disposed within the lumen and configured to:
occupy a longitudinal space in the lumen between the inner surface of the sheath body and the catheter device when the catheter device is disposed within the sheath and the balloon is inflated, and fluidically seal the lumen.

A2. The sheath according to A1, wherein the balloon forms an interference fit between the catheter device and the inner surface of the sheath body when inflated.

A3. The sheath according to any of A1-A2, wherein the balloon is positioned at least at the distal end of the sheath body.

A4. The sheath according to any of A1-A3, wherein the balloon is positioned along the entire length of the sheath body.

A5. The sheath according to any of A1-A4, wherein the balloon is attached to the inner surface of the sheath body.

A6. The sheath according to A5, wherein the balloon is attached at least at the distal end of the inner surface of the sheath body.

A7. The sheath according to A4, wherein the balloon is attached along the entire length of the inner surface of the sheath body.

A8. The sheath according to any of A5-A7, wherein the balloon is attached along at least a portion of the circumference of the sheath body.

A9. The sheath according to any of A5-A8, wherein the balloon is attached along at least any of the following portions of the sheath body: about 25%, about 50%, about 75%, about 100% of the inner circumference of the sheath body.

A10. The sheath according to any of A5-A9, wherein the inner surface of the sheath body is pretreated to improve attachment of the balloon to the inner surface of the sheath body.

A11. The sheath according to any of A5-A10, wherein the balloon is attached to the inner surface of the sheath body via heat or solvent bond.

A12. The sheath according to A10, wherein the inner surface of the sheath body is pretreated via any one of: plasma activation and coronary treatment.

A13. The sheath according to any of A11-A12, wherein the balloon is inflated via an inflation opening located on the inner surface of the distal end of the sheath body.

A14. The sheath according to A13, wherein the sheath body comprises an inflation lumen that extends from the proximal end of the sheath body to the inflation opening.

A15. The sheath according to A14, wherein the inflation lumen is in fluid communication with the inflation opening.

A16. The sheath according to any of A14-A22, wherein the inflation lumen extends along the length of the sheath body linearly or curvilinearly.

A17. The sheath according to any A1-A4, further comprising:
a balloon sleeve on which the inflatable balloon is attached, the sleeve aligned in-line with the catheter device and configured to traverse the lumen of the sheath body.

A18. The sheath according to A17, wherein the proximal end of the balloon sleeve comprises a hemostasis valve that seals with the catheter device.

A19. The sheath according to any of A17-A18, wherein the balloon sleeve comprises an inflation lumen in fluid communication with the balloon for inflation.

A20. The sheath according to A19, wherein the proximal end of the balloon sleeve comprises an inflation port in fluid communication with the inflation lumen for inflation.

A21. The sheath according to any A1-A16, wherein the proximal end of the sheath body is coupled to an inflation port that is in fluid communication with the balloon for inflation.

A22. The sheath according to any of A19-A21, wherein the inflation lumen is in communication with a fixed volume syringe for inflation of the balloon at the proximal end of the sheath body.

A23. The sheath according to any of A21-A22, wherein the balloon is inflated via the inflation port with any one of: water, saline and air.

A24. The sheath according to any of A1-A23, wherein the balloon is positioned in-line with the catheter device.

A25. The sheath according to any of A1-A24, wherein the balloon is radially symmetric with respect to the longitudinal axis of the sheath body.

A26. The sheath according to any of A1-A25, wherein the balloon is ring-shaped through which the catheter device traverses.

A27. The sheath according to any of A1-A26, wherein the balloon applies a radial force on the catheter device when inflated, thereby locking the catheter device in position.

A28. The sheath according to any of A1-A18, wherein the balloon is asymmetric with respect to the longitudinal axis of the sheath body.

A29. The sheath according to A28, wherein the balloon exerts a force on the catheter device so as to push the catheter device towards a portion of the inner surface of the sheath body when inflated, thereby locking the catheter device in position.

A30. The sheath according to any of A1-A29, wherein the sheath body comprises a lamination of a plurality of polymer layers arranged coaxially with each other about the longitudinal axis.

A31. The sheath according to any of A1-A29, wherein the sheath body comprises a combination of a plurality of tubular polymer layer portions arranged sequentially from the proximal to the distal end of the sheath body.

A32. The sheath according to any of A30-A31, wherein each polymer layer comprises a different polymer material type.

A33. The sheath according to A32, wherein the polymer material type comprises any one of: PEBAX® 7233SA, PEBAX® 7033SA, PEBAX® 6333SA, PEBAX® 5533SA, PEBAX® 3533SA, and PEBAX® 2533SA.

A34. The sheath according to any of A1-A33, wherein the sheath body comprises reinforced structures to prevent kinking.

A35. The sheath according A34, wherein the reinforced structures comprise any one of: braids, coils and laser cut features.

A36. The sheath according to any of A1-A35, wherein the balloon is fabricated from any one of: urethane, polyurethane, polyethylene, polypropylene, polyethylene terephthalate (PET), polyvinyl chloride (PVC), polyethylene, cross-linked polyethylene, a polyether block amide (PEBA), and nylon.

A37. The sheath according to any of A1-A36, wherein the sheath body is fabricated from any one of: a polyether block amide (such as PEBAX® or PebaSlix®), a polyethylene material, a polytetrafluoroethylene (PTFE) material, a high-density polyethylene (HDPE) material, a medium-density polyethylene (MDPE) material, and a low-density polyethylene (LDPE) material.

A38. The sheath according to any of A1-A37, wherein the distal end of the sheath body is fabricated from a softer elastic material than that used for the rest of the sheath body.

A39. The sheath according to A38, wherein the distal end of the sheath body comprises a smaller diameter so as to seal onto the catheter device.

A40. The sheath according to any of A17-A19, wherein the balloon sleeve is fabricated from any one of: urethane, polyurethane, polyethylene, polypropylene, polyethylene terephthalate (PET), polyvinyl chloride (PVC), polyethylene, cross-linked polyethylene, a polyether block amide (PEBA), and nylon.

A41. The sheath according to any of A1-A40, wherein the balloon is compliant and held flush against the inner surface of the sheath body when deflated.

A42. The sheath according to A1, wherein the balloon is non-compliant and not held flush against the inner surface of the sheath body when deflated.

A43. The sheath according to any of A1-A42, wherein the balloon is coated with a hydrophilic coating.

A44. The sheath according to any of A1-A42, wherein the balloon is coated with a hydrophobic coating.

A45. The sheath according to any of A1-A44, wherein the coating is of a thickness that ensures appropriate balloon inflation characteristics.

A46. The sheath according to any of A1-A45, wherein the sheath body deforms when the balloon is inflated, thereby fixing the position of the sheath in the arteriotomy of the patient.

A47. The sheath according to any of A1-A46, wherein the proximal end of the sheath is coupled to a hub for manipulating the sheath as it is positioned within the arteriotomy of the patient.

A48. The sheath according to any of A14-A16 and A19-A22, wherein the hub comprises an inflation sideport that is in fluid communication with the fluid lumen, thereby enabling the attachment of a source of balloon inflation fluid.

A49. The sheath according to any of A47-A48, wherein the hub comprises an irrigation port that is in fluid communication with the space between the catheter device and the inner surface of the sheath body, thereby enabling the space to be flushed with fluid prior to inflation of the balloon.

A50. A sheath kit for delivery of a catheter device to an arteriotomy of a patient, the sheath kit comprising:
a sheath according to any of A1-A49; and
a fixed volume syringe filled with fluid and coupled to the sheath for inflating the balloon with the fluid.

B1. A method of fabricating a sheath with an internal balloon, the method comprising the steps of:
providing a tubular sheath body, the sheath body having a longitudinal axis, an open proximal end, an open distal end, an outer surface and an inner surface, the inner surface defining a lumen between the proximal and distal ends for passage of a catheter device; and providing an inflatable balloon positioned in the lumen, the balloon configured to occupy a space in the lumen between the inner surface of the sheath body and the catheter device when the balloon is inflated thereby sealing the space from the arteriotomy.

B2. The method of B1, further comprising:

attaching the inflatable balloon to at least a portion of the inner surface of the sheath body.

B3. The method of any of B1-B2, further comprising the step of:

pretreating the inner surface of the sheath body to improve adhesion between the balloon and the inner surface of the sheath body.

B4. The method of B3, wherein the pretreatment comprises any one of: plasma activation and coronary treatment.

B5. The method of B1, further comprising:

providing a balloon sleeve for insertion into the lumen of the sheath body, the sleeve aligned in-line with the catheter device; and attaching the inflatable balloon to at least a portion of the sleeve.

B6. The method of any of B2-B5, wherein attachment of the balloon is carried out via heat or solvent bond.

B7. The method of any of B1-B6, further comprising the step of:

coating the surface of the balloon with either a hydrophilic coating or a hydrophobic coating.

B8. The method of B7, further comprising:

coating the surface of the balloon up to a predetermined coating thickness to achieve particular inflation characteristics of the balloon.

B9. The method of any of B1-B8, further comprising the step of:

coupling a proximal end of the sheath body to a hub.

C1. A method of fabricating a sheath with an internal balloon according to any of A1-A49.

D1. A method of using a sheath with an internal balloon for treating a patient with a catheter device, the method comprising the steps of:

positioning a sheath according to any one of A1-A49 in an arteriotomy of the patient;

inserting the catheter device into the lumen to position a distal end of the catheter device in the arteriotomy of the patient;

flushing the space with an irrigation fluid; and inflating the balloon with an inflation fluid so as to seal the space from the arteriotomy.

D2. A method of using a sheath according to D1, further comprising the step of:

inserting a balloon sleeve on which the inflatable balloon is attached into the lumen, the sleeve aligned in-line with the catheter device.

E1. A method of inserting a catheter based device through an arteriotomy of a patient, the method comprising the steps of:

inserting a sheath having a lumen running therethrough into the arteriotomy of the patient;

inserting the catheter based device into the lumen; and inflating a balloon within the lumen between the sheath and the catheter based device so as to fluidically seal the lumen.

E2. The method of E1, further comprising flushing the lumen prior to inflating the balloon.

E3. The method of any of E1-E2, wherein inserting the sheath comprises inserting a dilator into the lumen of the sheath for positioning the sheath into the arteriotomy of the patient.

E4. The method of any of E1-E3, wherein the balloon is attached to the sheath.

E5. The method of any of E1-E3, further comprising inserting a balloon sleeve, onto which the balloon is attached, into the lumen of the sheath between the sheath and the catheter based device, before inflating the balloon.

E6. The method of E5, wherein the balloon sleeve is tightly coaxially arranged around the catheter based device.

The invention claimed is:

1. An introducer sheath assembly comprising:

a tubular sheath body having a proximal end, a distal end, an outer surface, and an inner surface, the inner surface defining a lumen between the proximal and distal ends for passage of a catheter device;

a balloon sleeve having an inflatable balloon, the balloon sleeve configured to surround and slide over a portion of the catheter device for insertion into the lumen of the tubular sheath body such that the inflatable balloon forms a fluidic seal between the inner surface of the tubular sheath body and the catheter device when the inflatable balloon is inflated, the fluidic seal being configured to form a region in which fluid is prevented from flowing between the tubular sheath body and the catheter device.

2. The introducer sheath assembly of claim 1, wherein the inflatable balloon is configured to form an interference fit between the catheter device and the inner surface of the tubular sheath body when inflated, thereby preventing any axial movement of the catheter device relative to the tubular sheath body.

3. The introducer sheath assembly of claim 1, wherein a length of the inflatable balloon is configured such that a proximal end of the inflatable balloon will be aligned with the proximal end of the tubular sheath body when the balloon sleeve is inserted into the lumen of the tubular sheath body and a distal end of the inflatable balloon is aligned with the distal end of the tubular sheath body.

4. The introducer sheath assembly of claim 1, wherein a proximal end of the balloon sleeve is configured to remain proximal of the proximal end of the tubular sheath body when the balloon sleeve is inserted into the lumen of the tubular sheath body and a distal end of the inflatable balloon is aligned with the distal end of the tubular sheath body.

5. The introducer sheath assembly of claim 1, wherein the balloon sleeve comprises an inflation lumen that extends linearly or curvilinearly from a proximal end of the balloon sleeve to an inflation opening located within the inflatable balloon, wherein the inflation lumen is in fluid communication with the inflation opening.

6. The introducer sheath assembly of claim 1, wherein the inflatable balloon is radially symmetric with respect to a longitudinal axis of the balloon sleeve when inflated.

7. The introducer sheath assembly of claim 1, wherein the inflatable balloon is ring-shaped when inflated.

8. The introducer sheath assembly of claim 1, wherein the inflatable balloon is configured to apply a radial force on the catheter device when inflated, thereby locking the catheter device in a position relative to the tubular sheath body.

9. The introducer sheath assembly of claim 1, wherein the inflatable balloon is asymmetric with respect to a longitudinal axis of the balloon sleeve when inflated.

10. The introducer sheath assembly of claim 9, wherein the inflatable balloon is configured to exert a force on the catheter device so as to push the catheter device towards a portion of the inner surface of the tubular sheath body when inflated, thereby locking the catheter device in a position relative to the tubular sheath body.

11. The introducer sheath assembly of claim 1, wherein the distal end of the tubular sheath body comprises an elastic material that is softer than a material of a rest of the tubular sheath body.

12. The introducer sheath assembly of claim 1, wherein the balloon sleeve comprises a hub at a proximal end of the balloon sleeve.

13. The introducer sheath assembly of claim 12, wherein the hub comprises a hemostasis valve.

14. The introducer sheath assembly of claim 12, wherein the hub comprises an irrigation port that is configured to be in fluid communication with a space between the catheter device and an inner surface of the balloon sleeve, thereby enabling the space to be flushed with fluid prior to inflation of the inflatable balloon.

\* \* \* \* \*